(12) United States Patent
Chen et al.

(10) Patent No.: US 10,232,013 B2
(45) Date of Patent: Mar. 19, 2019

(54) USE OF AN ANTIMICROBIAL PEPTIDE TP4 IN TREATING A CANCER

(71) Applicant: Academia Sinica, Taipei (TW)

(72) Inventors: Jyh-Yih Chen, Taipei (TW); Chen-Hung Ting, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 15/403,595

(22) Filed: Jan. 11, 2017

(65) Prior Publication Data
US 2017/0340700 A1 Nov. 30, 2017

Related U.S. Application Data

(60) Provisional application No. 62/277,191, filed on Jan. 11, 2016.

(51) Int. Cl.
*A61K 45/06* (2006.01)
*A61K 45/00* (2006.01)
*A61K 38/17* (2006.01)
*A61K 38/00* (2006.01)

(52) U.S. Cl.
CPC .......... *A61K 38/1706* (2013.01); *A61K 45/06* (2013.01)

(58) Field of Classification Search
CPC .... A61K 38/1706; A61K 45/06; A61K 38/00; A61K 45/00; A61K 38/17
USPC ...................... 514/19.2, 19.3, 19.4, 19.8, 2.3
See application file for complete search history.

(56) References Cited

U.S. PATENT DOCUMENTS 5,595,756 A * 1/1997 Bally ................... A61K 9/1272
264/4.1
2016/0303190 A1* 10/2016 Chen .................. A61K 38/1706

OTHER PUBLICATIONS

Narayana et al, "Efficacy of the antimicrobial peptide TP4 against Helicobacter pylori infection: in vitro membrane perturbation via micellization and in vivo suppression of host immune responses in a mouse model," Oncotarget, May 11, 2015, 6(15): 12936-12954.*
Albini et al, "Cancer prevention by targeting angiogenesis," Nat. Rev. Clin. Oncol., Jul. 31, 2012, 1-12.*
Peng et al, "Five Different Piscidins from Nile Tilapia, Oreochromis niloticus: Analysis of Their Expressions and Biological Functions," PLOS One, Nov. 2012, 7(11): 1-12.*
Neidle, Stephen, ed, "Cancer Drug Design and Discovery," Elsevier/Academia Press, 2008, 427-431.*
Gura T., "Systems for Identifying New Drugs Are Often Faulty," Science, Nov. 7, 1997, 278: 1041-1042.*
Auerbach et al, "Angiogenesis assyas: Problems and pitfalls," Cancer and Metastasis Reviews, 2000, 19: 167-172.*
Jain RK, "Barriers to Drug Delivery in Solid Tumors," Scientific American, Jul. 1994, 58-65.*
Sporn et al, "Chemoprevention of cancer," Carcinogenesis, 2000, 21(3): 525-530.*

* cited by examiner

*Primary Examiner* — Julie Ha
(74) *Attorney, Agent, or Firm* — Juan Carlos A. Marquez; Marquez IP Law Office, PLLC

(57) ABSTRACT

The preset invention relates to a new approach for treating a cancer, particularly a malignant tumor, a multidrug-resistant (MDR) cancer, a recurrent cancer or a metastatic cancer, using a specific cationic antimicrobial peptide (CAP), tilapia piscidin 4 (TP4), which is derived from Nile Tilapia (*Oreochromis niloticus*). Also provided is a method for treating a breast cancer, particularly triple negative breast cancer (TNBC) with TP4.

2 Claims, 27 Drawing Sheets

Specification includes a Sequence Listing.

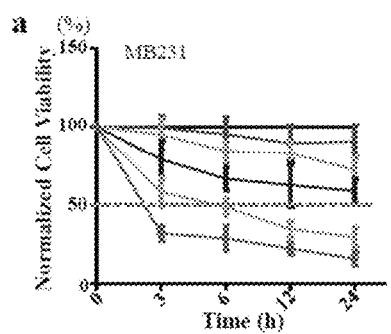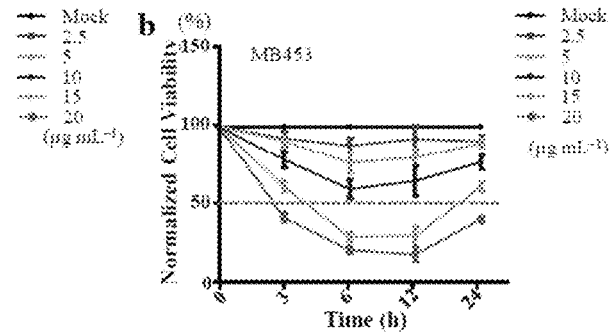
Figure 1a                    Figure 1b
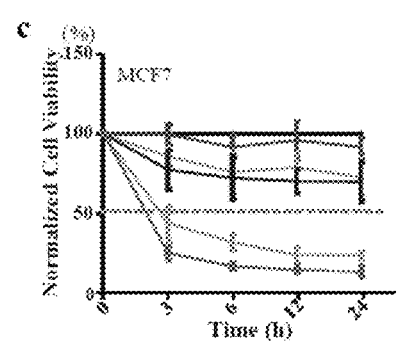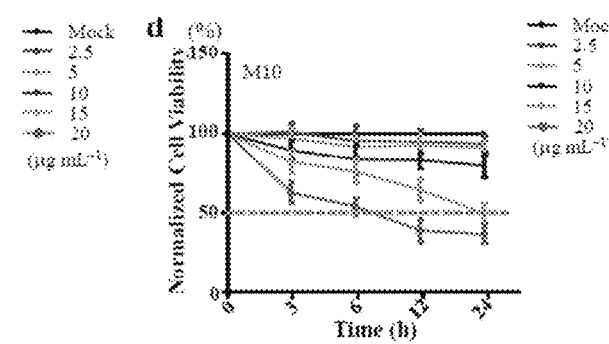
Figure 1c                    Figure 1d

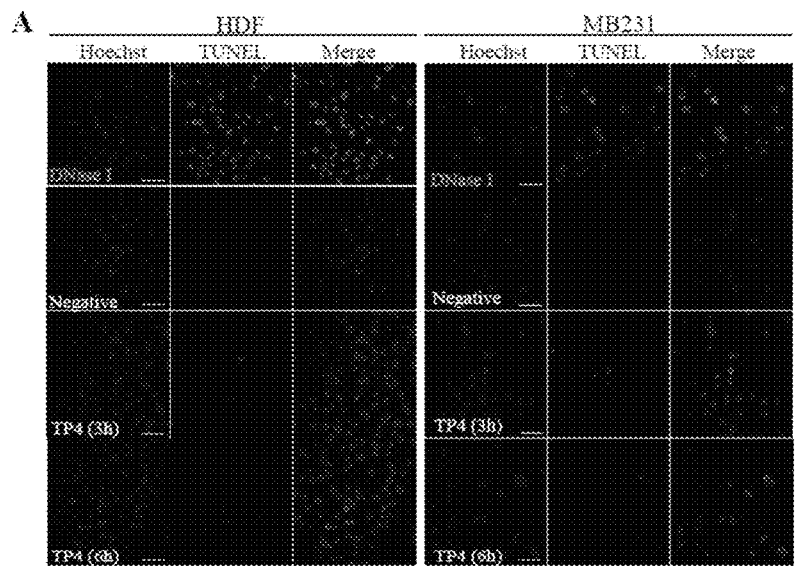
Figure 2A
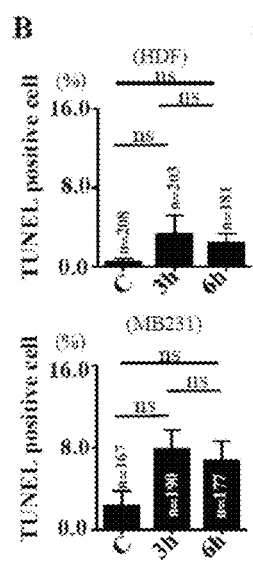 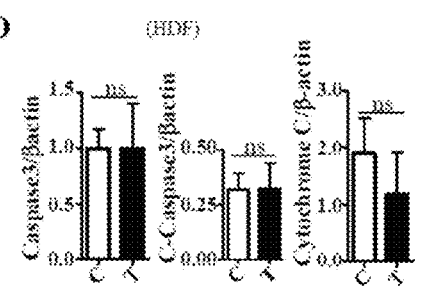 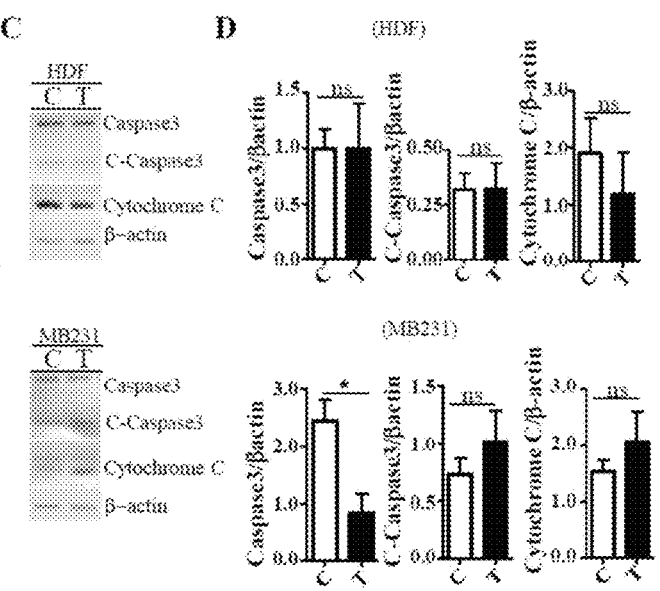
Figure 2B  Figure 2C  Figure 2D

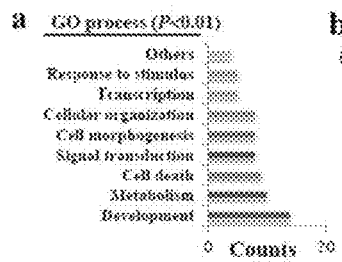
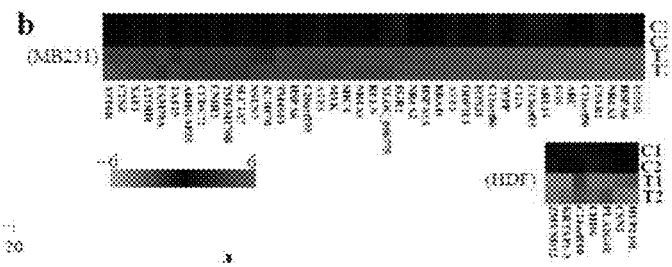
Figure 3a    Figure 3b
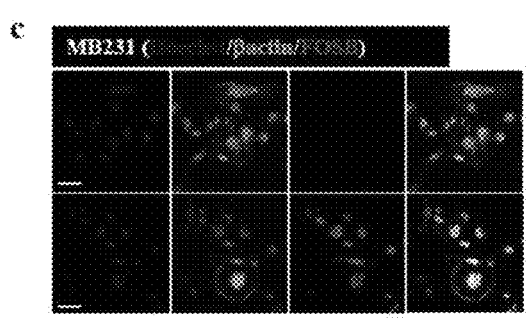
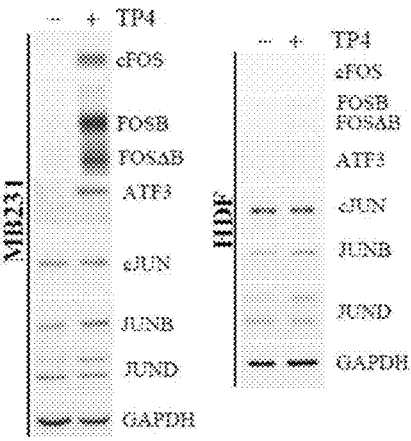
Figure 3c    Figure 3d
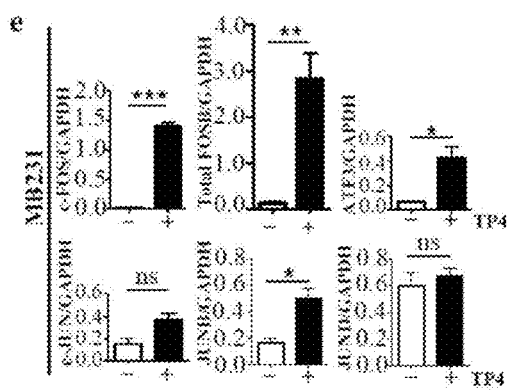
Figure 3e

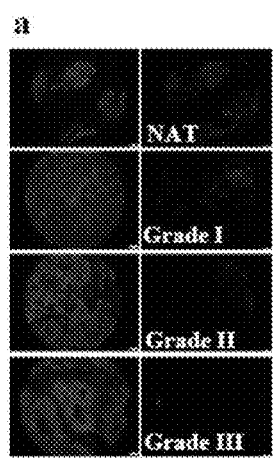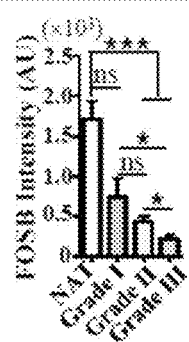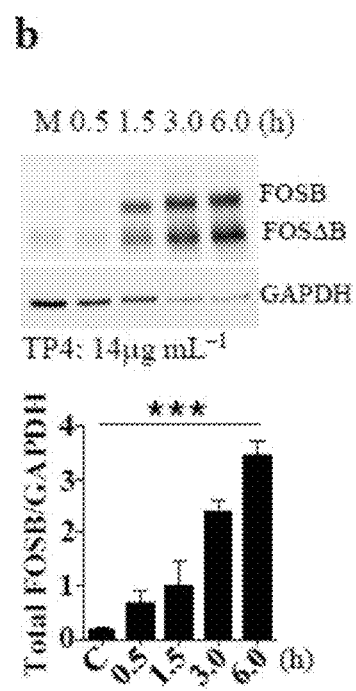
Figure 6a　　　　　　　Figure 6b

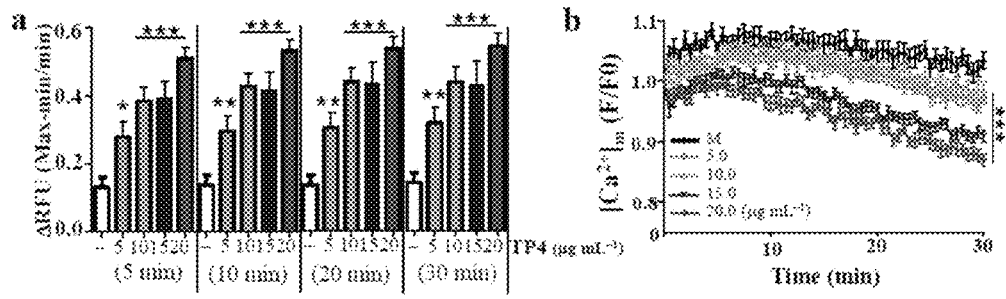
Figure 9a
Figure 9b
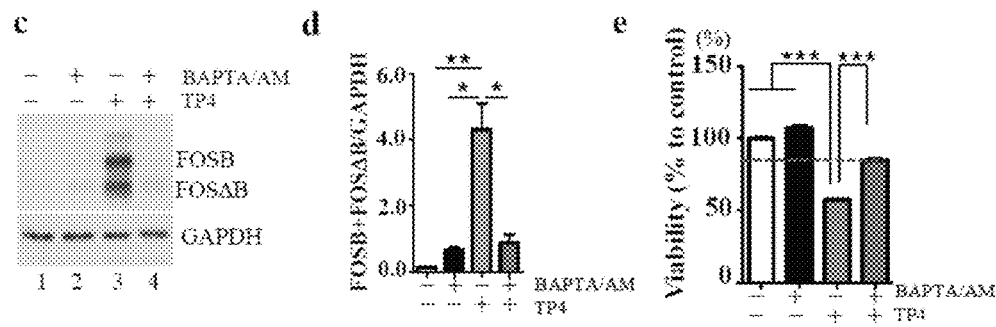
Figure 9c
Figure 9d
Figure 9e
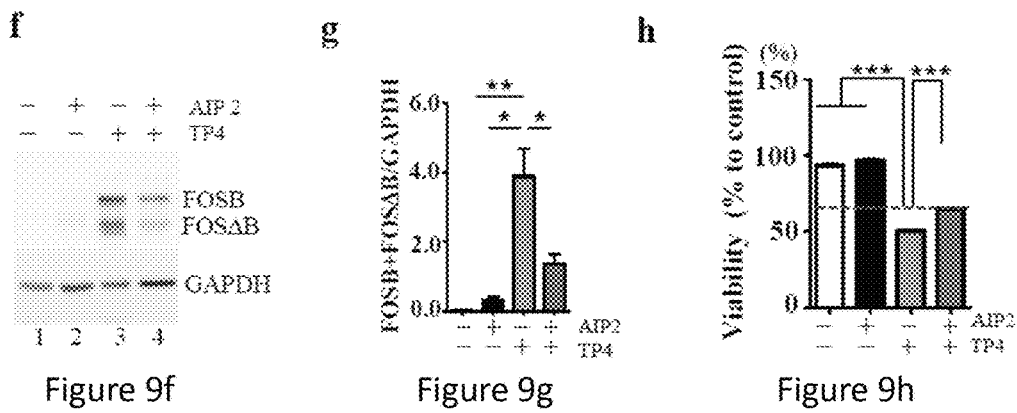
Figure 9f
Figure 9g
Figure 9h

SEQUENCE LISTING

```
<160> NUMBER OF SEQ ID NOS: 17

<210> SEQ ID NO 1
<211> LENGTH: 25
<212> TYPE: PRT
<213> ORGANISM: Oreochromis niloticus
<220> FEATURE:
<223> OTHER INFORMATION: TP4

<400> SEQUENCE: 1

Phe Ile His His Ile Ile Gly Gly Leu Phe Ser Ala Gly Lys Ala Ile
1               5                   10                  15

His Arg Leu Ile Arg Arg Arg Arg
            20                  25

<210> SEQ ID NO 2
<211> LENGTH: 19
<212> TYPE: DNA
<213> ORGANISM: Artificial Sequence
<220> FEATURE:
<223> OTHER INFORMATION: T4 F primer

<400> SEQUENCE: 2
```
ttccctctgg ctacctatg                                              19

<210> SEQ ID NO 3
<211> LENGTH: 20
<212> TYPE: DNA
<213> ORGANISM: Artificial Sequence
<220> FEATURE:
<223> OTHER INFORMATION: TP4 R primer

<400> SEQUENCE: 3
tcttgatggt ggcgattgcg                                             20

<210> SEQ ID NO 4
<211> LENGTH: 22
<212> TYPE: DNA
<213> ORGANISM: Artificial Sequence
<220> FEATURE:
<223> OTHER INFORMATION: TP4 F primer

<400> SEQUENCE: 4
ctcacttagg caaaatgacc ag                                          22

<210> SEQ ID NO 5
<211> LENGTH: 19
<212> TYPE: DNA
<213> ORGANISM: Artificial Sequence
<220> FEATURE:
<223> OTHER INFORMATION: TP4 R primer

<400> SEQUENCE: 5
ttccaatgcg tcggctttc                                              19

<210> SEQ ID NO 6
<211> LENGTH: 27
<212> TYPE: DNA
<213> ORGANISM: Artificial Sequence
<220> FEATURE:
<223> OTHER INFORMATION: TP4 F primer

<400> SEQUENCE: 6
ctatgacatc acagcatctt caaattc                                     27

<210> SEQ ID NO 7
<211> LENGTH: 18
<212> TYPE: DNA
<213> ORGANISM: Artificial Sequence
<220> FEATURE:
<223> OTHER INFORMATION: TP4 R primer

<400> SEQUENCE: 7 agtgttttggt cccagtt                                               18

<210> SEQ ID NO 8
<211> LENGTH: 19
<212> TYPE: DNA
<213> ORGANISM: Artificial Sequence
<220> FEATURE:
<223> OTHER INFORMATION: TP4 F primer

<400> SEQUENCE: 8
tttgtgggag acagacggt                                              19

<210> SEQ ID NO 9
<211> LENGTH: 20
<212> TYPE: DNA

```
<213> ORGANISM: Artificial Sequence
<220> FEATURE:
<223> OTHER INFORMATION: TP4 R primer

<400> SEQUENCE: 9
ccaactgctt cattttgtgc                                          20

<210> SEQ ID NO 10
<211> LENGTH: 20
<212> TYPE: DNA
<213> ORGANISM: Artificial Sequence
<220> FEATURE:
<223> OTHER INFORMATION: TP4 F primer

<400> SEQUENCE: 10
agcactccac aaccccaatc                                          20

<210> SEQ ID NO 11
<211> LENGTH: 19
<212> TYPE: DNA
<213> ORGANISM: Artificial Sequence
<220> FEATURE:
<223> OTHER INFORMATION: TP4 R primer

<400> SEQUENCE: 11 gaccccctttt tccttcatc                                          19

<210> SEQ ID NO 12
<211> LENGTH: 18
<212> TYPE: DNA
<213> ORGANISM: Artificial Sequence
<220> FEATURE:
<223> OTHER INFORMATION: TP4 F primer

<400> SEQUENCE: 12
catccgcaac tacaagac                                            18

<210> SEQ ID NO 13
<211> LENGTH: 18
<212> TYPE: DNA
<213> ORGANISM: Artificial Sequence
<220> FEATURE:
<223> OTHER INFORMATION: TP4 R primer

<400> SEQUENCE: 13
tcacctggag gataagcg                                            18

<210> SEQ ID NO 14
<211> LENGTH: 20
<212> TYPE: DNA
<213> ORGANISM: Artificial Sequence
<220> FEATURE:
<223> OTHER INFORMATION: TP4 F primer

<400> SEQUENCE: 14
tcttcaaagt cgggtgtatg                                          20

<210> SEQ ID NO 15
<211> LENGTH: 21
<212> TYPE: DNA
<213> ORGANISM: Artificial Sequence
<220> FEATURE:
<223> OTHER INFORMATION: TP4 R primer

<400> SEQUENCE: 15
ggtcatctct ccagtctaag g                                        21
```

```
<210> SEQ ID NO 16
<211> LENGTH: 19
<212> TYPE: DNA
<213> ORGANISM: Artificial Sequence
<220> FEATURE:
<223> OTHER INFORMATION: TP4 F primer

<400> SEQUENCE: 16
gccaaacgaa gaaggtcag                                               19

<210> SEQ ID NO 17
<211> LENGTH: 18
<212> TYPE: DNA
<213> ORGANISM: Artificial Sequence
<220> FEATURE:
<223> OTHER INFORMATION: TP4 R primer

<400> SEQUENCE: 17
caccgccaac ccatttca                                                18
```

USE OF AN ANTIMICROBIAL PEPTIDE TP4 IN TREATING A CANCER

RELATED APPLICATION

The present application claims priority under 35 U.S.C. § 119(e) to U.S. Provisional Patent Application No. 62/277,191, filed Jan. 11, 2016, the content of which is herein incorporated by reference in its entirety.

A sequence listing as an ASCII text file named "ACA0110US-Sequence Listing.txt" is attached and is being submitted concurrently herewith. Said sequence listing ASCII text file was created on Jan. 10, 2017 and is 4 KB in size. The entire content of said sequence listing ASCII text file is incorporated herein by reference.

FIELD OF THE INVENTION

The present invention relates to a new method for treating a cancer, particularly triple-negative breast cancer (TNBC), with an antimicrobial peptide TP4.

BACKGROUND OF THE INVENTION

Breast cancer (BC) is the most common malignancy that causes death in women. Global gene-expression profile studies have classified breast cancers into different subtypes, among which, the subtypes lacking expression of estrogen receptors (ER), progesterone receptors (PR), and human epidermal growth factor receptor 2 (HER2) are clustered as triple negative BC (TNBC:ER$^-$/PR$^-$/HER2$^-$). Hormone or targeted therapies are not usually effective against TNBC, but systemic treatment, such as anthracycline or taxane-based conventional chemotherapy, demonstrates strong therapeutic efficacy (Rouzier et al. Breast cancer molecular subtypes respond differently to preoperative chemotherapy. *Clinical cancer research: an official journal of the American Association for Cancer Research* 11, 5678-5685, 2005; Carey et al. The triple negative paradox: primary tumor chemosensitivity of breast cancer subtypes. *Clinical cancer research: an official journal of the American Association for Cancer Research* 13, 2329-2334, 2007). However, TNBC patients often present with distant metastases and have poor prognosis. The main cause of chemotherapeutic agent failure is the development of multidrug-resistant (MDR) cancer cells under standard chemotherapeutic regimens; in addition, such regimens damage healthy cells, causing adverse side-effects. Use of non-cross-resistant drugs or biological agents in combination with chemotherapeutic drugs is a possible option for TNBC patients with metastases. However, the prognosis of metastatic TNBC patients remains poor even though such options improve the outcome.

Several studies have indicated that some metastatic cancer cells that respond poorly to treatment possess negatively-charged phosphatidylserine (PS) or anionic structures on their outer membrane, in contrast to healthy cells that are normally zwitterionic. This characteristic allows some selective cytotoxic agents, such as cationic antimicrobial peptides (CAPs), to attack cancers through electrostatic interactions (Hallock et al., Membrane composition determines pardaxin's mechanism of lipid bilayer disruption. *Biophysical journal* 83, 1004-1013, 2002; Gottler & Ramamoorthy, Structure, membrane orientation, mechanism, and function of pexiganan—a highly potent antimicrobial peptide designed from magainin. *Biochimica et biophysica acta* 1788, 1680-1686, 2009; and Ramamoorthy et al., Cholesterol reduces pardaxin's dynamics—a barrel-stave mechanism of membrane disruption investigated by solid-state NMR. *Biochimica et biophysica acta* 1798, 223-227, 2010). Cationic antimicrobial peptides (CAPs) are evolutionarily conserved components of the innate immune system, integral for activity against a broad range of pathogens (Zasloff, Antimicrobial peptides of multicellular organisms. *Nature* 415, 389-395, 2002; and Zanetti, Cathelicidins, multifunctional peptides of the innate immunity. *Journal of leukocyte biology* 75, 39-48, 2004). The defensive capabilities of CAPs arise from their structures, which allow them to penetrate anionic bacterial membrane (Powers J P, Hancock R E. The relationship between peptide structure and antibacterial activity. *Peptides* 24, 1681-1691, 2003). In addition to their antibacterial activities, some CAPs are cytotoxic to certain cancer types, but are less toxic to normal cells (Papo et al., A novel lytic peptide composed of DL-amino acids selectively kills cancer cells in culture and in mice. *The Journal of biological chemistry* 278, 21018-21023, 2003; Hoskin & Ramamoorthy, Studies on anticancer activities of antimicrobial peptides. *Biochimica et biophysica acta* 1778, 357-375, 2008; and Ting et al., The mechanisms by which pardaxin, a natural cationic antimicrobial peptide, targets the endoplasmic reticulum and induces c-FOS. *Biomaterials* 35, 3627-3640, 2014). Treatment of cancer cells with large amounts of CAPs leads to transient membrane lysis (Hilchie et al., Pleurocidin-family cationic antimicrobial peptides are cytolytic for breast carcinoma cells and prevent growth of tumor xenografts. *Breast cancer research: BCR* 13, R102, 2011; Papo et al., Suppression of human prostate tumor growth in mice by a cytolytic D-, L-amino Acid Peptide: membrane lysis, increased necrosis, and inhibition of prostate-specific antigen secretion. *Cancer research* 64, 5779-5786, 2004; Rodrigues et al. Effective topical treatment of subcutaneous murine B16F10-Nex2 melanoma by the antimicrobial peptide gomesin. *Neoplasia* 10, 61-68, 2008; Chen et al., A fish antimicrobial peptide, tilapia hepcidin TH2-3, shows potent antitumor activity against human fibrosarcoma cells. *Peptides* 30, 1636-1642, 2009; Lin et al., Epinecidin-1, an antimicrobial peptide from fish (*Epinephelus coioides*) which has an antitumor effect like lytic peptides in human fibrosarcoma cells. *Peptides* 30, 283-290, 2009; Gaspar et al., Anticancer peptide SVS-1: efficacy precedes membrane neutralization. *Biochemistry* 51, 6263-6265, 2012; Wang et al., Antitumor effects and cell selectivity of temporin-1CEa, an antimicrobial peptide from the skin secretions of the Chinese brown frog (*Rana chensinensis*). *Biochimie* 94, 434-441, 2012). However, low concentrations of CAPs can trigger apoptosis (Kawamoto et al., A novel transferrin receptor-targeted hybrid peptide disintegrates cancer cell membrane to induce rapid killing of cancer cells. *BMC cancer* 11, 359 (2011; and Huang & Chen, Proteomic analysis reveals that pardaxin triggers apoptotic signaling pathways in human cervical carcinoma HeLa cells: cross talk among the UPR, c-Jun and ROS. *Carcinogenesis* 34, 1833-1842, 2013), and/or necrosis of cancer cells (Papo et al.; Leuschner et al., Membrane disrupting lytic peptide conjugates destroy hormone dependent and independent breast cancer cells in vitro and in vivo. *Breast cancer research and treatment* 78, 17-27, 2003; Leuschner & Hansel, Targeting breast and prostate cancers through their hormone receptors. *Biology of reproduction* 73, 860-865, 2005; van Zoggel H, et al. Antitumor and angiostatic activities of the antimicrobial peptide dermaseptin B2. *PloS one* 7, e44351, 2012). CAPs have been reported to induce several intracellular events, including changes in calcium homeostasis, mitochondrial dysfunction, and induction of activator protein-1 (AP-1) (Hilchie et al.; Ting et al.;

Huang & Chen; and Wang et al. Rapid cytotoxicity of antimicrobial peptide tempoprin-1CEa in breast cancer cells through membrane destruction and intracellular calcium mechanism. *PloS one* 8, e60462. 2013). Calcium signaling appears to be activated early on in response to CAPs-induced stress, and mediates downstream activator protein-1 (AP-1) signaling (Ting et al.). AP-1 members are critical mediators of several pathways; these proteins form a dimer with proteins of the JUN proto-oncogene (c-JUN) family (c-JUN, JUNB, JUND) or FBJ murine osteosarcoma viral oncogene homolog (FOS) family (c-FOS, FOSB, FRA1/2). The dimer composition of AP-1 regulates downstream gene expression in response to cellular stimuli or in different cellular contexts, as well as controlling cell fate decisions (Eferl & Wagner, AP-1: a double-edged sword in tumorigenesis. *Nature reviews Cancer* 3, 859-868, 2003). FRA1 regulates tumor cell growth and metastasis through repression of CDH1 in poorly differentiated TNBC cells (Milde-Langosch, et al., The role of the AP-1 transcription factors c-Fos, FosB, Fra-1 and Fra-2 in the invasion process of mammary carcinomas. *Breast cancer research and treatment* 86, 139-152, 2004; and Zhao et al., Genome-wide profiling of AP-1-regulated transcription provides insights into the invasiveness of triple-negative breast cancer. *Cancer research* 74, 3983-3994, 2014), which lack FOSB expression (Bamberger et al., Expression pattern of the AP-1 family in breast cancer: association of fosB expression with a well-differentiated, receptor-positive tumor phenotype. *International journal of cancer Journal international du cancer* 84, 533-538, 1999; and Milde-Langosch et al., FosB is highly expressed in normal mammary epithelia, but downregulated in poorly differentiated breast carcinomas. *Breast cancer research and treatment* 77, 265-275, 2003). However, little is known about the role of FOSB in TNBC.

It is still desirable to develop a new therapy for cancer through other targets.

SUMMARY OF THE INVENTION

It is unexpectedly found that a specific cationic antimicrobial peptide (CAP), tilapia piscidin 4 (TP4), which is derived from Nile Tilapia (*Oreochromis niloticus*) is potential for treatment of a cancer, particularly triple negative breast cancer (TNBC).

In one aspect, the invention provides a method for treating a cancer in a subject, comprising administering to the subject a composition comprising a therapeutically effective amount of TP4, together with a pharmaceutically acceptable carrier.

In one embodiment of the invention, the method is effective in treatment of a cancer through induction of FBJ murine osteosarcoma viral oncogene homolog B (FOSB).

In one example, the cancer is a breast cancer, particularly triple negative breast cancer (TNBC).

In another aspect, the invention provides a method for controlling tumor cell growth in a subject suffering from a malignant tumor, comprising administering to the subject a composition comprising a therapeutically effective amount of TP4, together with a pharmaceutically acceptable carrier.

In further aspect, the invention provides a method for treating a multidrug-resistant (MDR) cancer in a subject, comprising administering to the subject a composition comprising a therapeutically effective amount of TP4, together with a pharmaceutically acceptable carrier.

In yet aspect, the invention provides a method for treating a metastatic cancer in a subject suffering from a cancer, comprising administering to the subject a composition comprising a therapeutically effective amount of TP4, together with a pharmaceutically acceptable carrier.

In further yet aspect, the invention provides a method for treating a subject suffering from a metastatic cancer in which the cancer cells possess negatively-charged phosphatidylserine (PS) or anionic structures on their outer membrane, comprising administering to the subject a composition comprising a therapeutically effective amount of TP4, together with a pharmaceutically acceptable carrier.

In one embodiment of the invention, a method for treating a recurrent cancer in a subject suffering from a cancer is provided. The method comprises administering to the subject a composition comprising a therapeutically effective amount of TP4, together with a pharmaceutically acceptable carrier.

In one more aspect, the invention provides a method for treating a subject with a malignant tumor, a MDR cancer, a recurrent cancer or a metastatic cancer, comprising administering to the subject a composition comprising a therapeutically effective amount of TP4 in combination with one or more anti-cancer drugs at a ratio to provide a synergistic effect in treating the cancer.

On the other hand, the invention provides a use of TP4 for manufacturing a medicament for treating a cancer, particularly TNBC.

Particularly, the cancer is a malignant tumor, a MDR cancer, a recurrent cancer or a metastatic cancer. The subject may be one suffering from a metastatic cancer in which the cancer cells possess negatively-charged phosphatidylserine (PS) or anionic structures on their outer membrane.

In further yet aspect, the invention provides a pharmaceutical composition for treating a malignant tumor, a MDR cancer, a recurrent cancer or a metastatic cancer, comprising a therapeutically effective amount of TP4, together with a pharmaceutically acceptable carrier.

In one further yet aspect, the invention provides a pharmaceutical composition for treating a malignant tumor, a MDR cancer, a recurrent cancer or a metastatic cancer, comprising a therapeutically effective amount of TP4 in combination with one or more anti-cancer drugs at a ratio to provide a synergistic effect in treating the cancer.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment which is presently preferred. It should be understood, however, that the invention is not limited to this embodiment.

In the drawings:

FIGS. 1*a*-1*e* show that TP4 selectively killed breast cancer cells through inducing necrosis in terms of the viability of the cells, including (*a*) MB231 (FIG. 1*a*), (*b*) MB453 (FIG. 1*b*), (*c*) MCF7 (FIG. 1*c*), (*d*) M10 (FIG. 1*d*), and (*e*) HDF (FIG. 1*e*), which were determined by MTS assay following treatment with varying doses of TP4 (2.5-20 μg mL$^{-1}$) at the indicated time-points (3-24 h). Sextuplicate wells were analyzed for each assay. Results represent the mean±SD (n=3, statistical analyses are shown in Table 1).

FIGS. 2A-2D show that TP4 did not trigger apoptosis.

FIG. 2A shows that TUNEL staining was used to evaluate apoptotic cell death in HDF (left) or MB231 (right) cells treated with TP4 (14 µg/mL) for 3 or 6 h. DNase I: positive control for DNA fragmentation. Bar: 50 µm.

FIG. 2B shows the results of the quantitation of the TUNEL-positive signals shown in FIG. 2A, indicating that a very limited number of cells exhibit fluorescent labeling. Results represent the mean±SEM (Student's t-test: ns: not significant).

FIG. 2C shows total lysates from HDF and MB231 cells incubated with (T) or without (C) TP4 were analyzed by Western blot using antibodies against Caspase3, cleaved Caspase3, Cytochrome C, and β-actin.

FIG. 2D shows the results of the quantitative analyses of the blots shown in FIG. 2C, using β-actin as a control for normalization. Results represent the mean±SEM from three independent experiments performed in triplicate (Student's t-test: *, P<0.05, ns: not significant).

FIGS. 3a-3h show the effects of TP4 in induction of FOSB in breast cancer cells.

FIG. 3a shows the result of gene ontology (GO) analyses of the microarray study classified dysregulated genes into nine defined categories (P<0.01); wherein the graph shows the number of genes of each category that were found to be differentially expressed in MB231 cells following TP4 treatment, as compared to untreated controls. Annotation terms were determined using David 6.7 software.

FIG. 3b shows the heat maps depicting the changes of expression of affected genes in MB231 or HDF cells following TP4 treatment (scale bar indicates log$_2$-fold changes). AP-1 transcription factor members are shown in red. C1, C2 and T1, T2 indicate the mock and TP4-treated samples collected from two independent assays, respectively.

FIG. 3c shows that TP4-(14 µg mL$^{-1}$) or mock-treated cells were stained with FOSB antibody (red) and βactin (green). Hochest 33342 dye was used for nuclear staining (blue). Bar: 50 µm.

FIG. 3d shows the total lysates from MB231 (left) or HDF (right) cells without (−) or with TP4 treatment (+), which were analyzed by Western blot using antibodies against GAPDH and FOS/JUN family proteins.

FIGS. 3e and 3f provides the results of the quantitative analysis of the blots shown in FIG. 3d using GAPDH as a control for normalization. Results represent the mean±SEM (n=3, Student's t-test: *, P<0.05 and **, P<0.01 versus control, ns: not significant).

FIG. 3g shows total lysates from control cells (lane 1), and cells treated with TP4 (lane 2), doxorubicin (lane 3), epirubicin (lane 4), docetaxel (lane 5), or paclitaxel (lane 6), which were analyzed by Western blot using antibodies against GAPDH and FOSB. The relative amounts of FOSB plus FOSAB in each lane are expressed as relative densitometric units (RDUs), calculated by dividing the FOSB plus FOSAB signal by the GAPDH signal.

FIG. 3h shows the results of MTS assay to measure cell viability in cells treated with PD98059 and TP4. Sextuplicate wells were analyzed for each assay. Results represent the mean±SEM (n=3). Statistical comparisons of the differences between groups treated with or without PD98059 were performed using Student's t-test. ns: not significant; *, P<0.05; ***, P<0.001.

FIG. 5A shows total lysates from MB231 and HDF cells treated with (T) or without (C) TP4, which were analyzed by Western blot using antibodies against ERK, phospho-ERK, JNK, phospho-JNK, p38, phospho-p38, and β-actin.

FIGS. 5B and 5C show the results of the quantitative analyses of the blots shown in FIG. 5A, using β-actin as a control for normalization. Results represent the mean±SEM from three independent experiments performed in triplicate (Student's t-test: **, P<0.01, ns: not significant).

FIGS. 6a-6k show that TP4 triggers TNBC cell death through FOSB induction.

FIG. 6a shows that normal adjacent tissue (NAT, n=26) and different grades of TNBC samples (n=6, 19, 10 for grade I, II, III samples, respectively) were stained with FOSB (red) antibody and Hochest 33342 (blue). Bar: 200 µm. Bottom graph, quantitation of the FOSB fluorescent signal indicated that FOSB level is associated with TNBC pathological grade. AU: arbitrary unit.

FIG. 6b shows total lysates from mock (M) and TP4-treated groups were examined by Western blot. Bottom graph, quantitative analysis of total FOSB (FOSB plus FOSAB) induction, normalized to GAPDH.

FIG. 6c shows the phase contrast and fluorescent images of MB231 cells transfected with FOSB or FOSAB vector. Bar: 50 µm. Cell viability was determined by ATP assay. At least fourteen replicate wells were analyzed for each dose.

FIG. 6d shows total lysates from mock and TP4-treated (14 µg mL$^{-1}$, 6 h) MB231 cells transduced with control or FOSB shRNA lentivirus were analyzed by Western blot.

FIG. 6e shows the induction of FOSB levels, as normalized to GAPDH.

FIG. 6f shows the effect of TP4 treatment on the viability of the indicated cells, as determined by MTS assay. Sextuplicate wells were analyzed for each assay.

FIG. 6g shows total lysates from MB231 cells (mock (−) or TP4-treated (+)) were analyzed by Western blot.

FIGS. 6h and 6i show the results of the quantitative analyses of FRA1 (FIG. 6h) and CDH1 (FIG. 6i) levels, normalized to GAPDH.

FIG. 6j shows that DNA-protein complexes were immunoprecipitated from mock (M−) or TP4-treated (T−) MB231 nuclear extracts (NEs) using the indicated antibodies. Forty picomoles of wild-type (WT) or mutated (MT) AP-1-binding oligonucleotides were used in the competition assay. K-562 cell NEs stimulated with TPA were used as a positive control.

FIGS. 6k and 6l show that cJUN was immunoprecipitated from mock (C) or TP4-treated (T) NE with anti-cJUN antibody. Total lysates from mock or TP4-treated groups were used as positive controls. Immunoprecipitation with nonspecific IgG was performed as a negative control. Coimmunoprecipitation of FRA1 (FIG. 6k) and FOSB (FIG. 6l) with cJUN were examined by Western blot. Results represent mean±SEM (n=3) by Student's t-test (a, d, e, h-j), one-way ANOVA (b), or two-way ANOVA (c). *, P<0.05; , P<0.01; *, P<0.001, ns: not significant.

FIGS. 7a-7e show the cellular localization of biotinylated-TP4 in MB231 (FIGS. 7a-7c) and HDF cells (FIG. 7d); wherein the cells were stained with biotin (green), Golgi marker (giantin; red) (FIGS. 7a, 7d), ER marker (calreticulin; red) (FIG. 7b), and mitochondrial marker (mitotracker; red) (FIG. 7c) antibodies. The plasma membrane was labeled with Alexa Flour-647-conjugated WGA (purple). Hoechst 33342 was used for nuclei staining (blue). Boxed regions are shown magnified in the panels to the right of the merged images. Yellow and white arrows indicate co-localization of biotinylated-TP4 with plasma membrane and Golgi or mitochondria, respectively. Bar: 50 μm.

FIGS. 7e and 7f show the results of the quantitation of the fluorescent signals, indicating that mitochondrial membrane potential was significantly decreased in TP4-treated MB231 cells (FIG. 7e). Statistical comparisons between mock and TP4-treated cells were performed using Student's t-test. ns: not significant; *, P<0.05; ***, P<0.001.

FIG. 7g shows the results of the quantitation of the fluorescent intensity in vehicle control (V), eGFP-transfected, and FOSB-transfected MB231 cells, indicating that mitochondrion fluorescent intensity was decreased in FOSB-transfected MB231 cells. Statistical comparisons between mock and TP4-treated groups were performed using Student's t-test. ns: not significant; ***, P<0.001.

FIG. 7h shows the results of the quantitation of the mitochondria fluorescent signals in Controlsh- and FOSBsh-MB231 cells treated with TP4 (14 μg m$^{-1}$ L for 0.5-6.0 h), indicating that mitochondrion intensity could be partially restored in FOSB-knockdown MB231 cells by T4 treatment. Statistical comparisons between mock and TP4 treatment groups were performed using Student's t-test (n=50 in each group). ns: not significant; *, P=0.0221; , P<0.01; *, P<0.001. AU: arbitrary unit.

FIGS. 8A and 8B shows that the MB231 and HDF cells were treated with TP4 (14 μg/mL) for 3 or 6 h and mitochondria were detected by staining with MitoTracker Red CMX-ROS dye. Hoechst33342 was used for nuclei staining (blue).

FIGS. 8C, 8D, 8E show that MB231 cells were stained by MitoTracker Red CMX-ROS dye; wherein FIG. 8D shows the MB231 cells expressing eGFP, as similar to the mitochondrial staining patterns to those shown in FIG. 8(C).

FIG. 8E shows MB231 cells expressing FOSB-tGFP with a decrease of mitochondrial intensity as compared with non-transfected cells. MT: MitoTracker. Scale bar: 50 μm.

FIGS. 8F and 8G show that Contsh-MB231 (FIG. 8(F)) and FOSBsh-MB231 (FIG. 8G, indicated by arrows) cells were treated with TP4 (14 μg/mL) for 0.5-6 h. Mitochondria (red) were detected by staining with MitoTracker Red CMX-ROS dye. Hoechst33342 was used for nuclei staining (blue). Boxed regions are shown magnified in the boxes to the right of the merged figures. Bar: 30 μm.

FIG. 9a-9i show that FOSB induction in TNBC cells requires calcium signaling.

FIG. 9a shows that $Ca^{2+}$ levels were measured by the addition of fluorescent $Ca^{2+}$ indicator (Fluo-4 NW) after treatment with the indicated doses of TP4 for 5-30 min. Octuplicate wells were analyzed for each assay. Results represent the mean±SEM (n=3, Student's t-test: *, P<0.05; , P<0.01; *, P<0.001).

FIG. 9b shows that mitochondrial $Ca^{2+}$ levels were measured kinetically using a fluorescent $Ca^{2+}$ indicator (Rhod-2 AM) after treatment with the indicated doses of TP4 every 30 sec for 30 min. Results represent the mean±SEM (n=3, one-way ANOVA: ***, P<0.001).

FIGS. 9c and 9f show total lysates from control (lane 1), BAPTA/AM (calcium chelator)-treated or AIP2 (CaMKII inhibitor)-treated cells (lane 2), TP4-treated cells (lane 3), and combination-treated cells (lane 4), which were analyzed by Western blot, using antibodies against GAPDH and FOSB.

FIGS. 9d and 9g show the results of the quantitative analyses of the blots shown in FIGS. 9c and 9f; levels of FOSB plus FOSAB were normalized to GAPDH. Results represent the mean±SEM (n=3, Student's t-test: *, P<0.05; **, P<0.01).

FIGS. 9e and 9h shows the cell viability, which was measured in cells treated with $Ca^{2+}$ chelator or CaMKII inhibitor and TP4. Sextuplicate wells were analyzed for each assay. Results represent the mean±SEM. Statistical comparisons of the differences between groups treated with or without inhibitors were performed using Student's t-test. ***, P<0.001.

FIG. 9i shows the proposed mechanism-of-action of TP4 against TNBC. TP4 targets the cell membrane and selectively targets the mitochondria. This in turn results in Ca2+ release and induction of FOSB expression. The FOSB/c-JUN becomes the predominant AP-1 complex that mediates downstream effects on cell death.

FIG. 10A shows that nude mice (n=5) were subcutaneously injected with 10 μL KY jelly plus 50 μL distilled water every two days for a total of fourteen injections.

FIG. 10B shows the size of the injection mixture, which was calculated every two days. Results represent the mean±SEM.

FIG. 11a shows xenograft growth in nude mice (n=5).

FIG. 11b shows the results of the quantitation of tumor size at the indicated days after the commencement of TP4 treatment. Statistical comparisons between KY and TP4-treated groups were performed by two-way ANOVA with post hoc analysis (Bonferroni test). ns: not significant; *, P<0.05; , P<0.01; *, P<0.001.

FIG. 11c shows xenograft tumor weight (left) and mouse body weight (right), which were determined when the mice were sacrificed (Student's t-test, **, P<0.01; ns, not significant).

FIG. 11d shows H&E staining of xenograft tumors. White dotted lines mark necrotic regions.

FIG. 11e shows the immunohistochemical staining of Ki-67-positive cells in xenograft tumors. Bar: 200 μm.

FIG. 14a shows the survival analysis of M10 and TNBC cells with or without TP4 treatment. Statistical comparisons were performed by Log-rank test. *, P<0.05; ***, P<0.001.

FIG. 14b shows the results of the quantitation of the eGFP fluorescent signals in M10 and TNBC xenografts with or without TP4 treatment (3 µg mL$^{-1}$ for 5 d). Statistical comparisons between mock and TP4-treated cells were performed using Student's t-test (n=11). ns: not significant; ***, P<0.001. AU: arbitrary unit.

FIG. 14c shows that transgenic zebrafish (fli:eGFP) with mOrange2-expressing TNBC xenografts (red) underwent mock or TP4 treatment (3 µg mL$^{-1}$ for 5 d) and were then stained with FOSB antibody (white). Each panel is a merged image of photographs taken of the posterior and anterior parts. Boxed regions are shown magnified in the lower-right corner of the figures. Blue arrows indicate disseminated tumor foci. Yellow arrows indicate TNBC xenografts with positive FOSB signals. Bar: 200 µm.

FIGS. 14d and 14e show the results of the quantitation of the primary tumor area (FIG. 14(d)) and disseminated tumor foci (FIG. 14(e)) in TNBC xenograft zebrafish. Results represent mean±SEM, and were analyzed by Student's t-test (n=4 in each group). ns: not significant; *, P=0.0221; , P<0.01; *, P<0.001.

FIG. 14f shows the time-lapse study of transgenic zebrafish (fli:eGFP) with mOrange2-expressing TNBC xenografts (red) during a single treatment with TP4 (3 µg/mL). Time series images were taken every 1 h, including z-stacks. Selected planes within 48 hrs are shown. Arrows in xenograft zebrafish indicate blood vessel invasion of TNBC cells. Boxed regions are shown magnified in the images above the figures.

FIG. 14g provides a schematic drawing of TNBC xenograft migration through the common cardinal vein (CCV) in zebrafish.

FIG. 14h shows the survival analysis of TNBC xenografts with or without TP4 (3 µg/mL, single treatment) at 72-120 hpf. Statistical comparisons of survival curves between groups were performed by Log-rank test. *, P<0.05.

FIGS. 14i and 14j show the results of the quantitation analysis of xenograft tumor growth, based on normalized tumor area (FIG. 14i) and fluorescence intensity (FIG. 14j), in zebrafish with or without TP4 treatment. Results represent mean±SD, and were analyzed by two-way ANOVA; ***, P<0.001.

FIG. 15A shows that a series of 13 doses of TP4 were added to fish water containing zebrafish at 48 hpf every day. Survival rates were determined (n=32 in each group).

FIGS. 15B and 15C show that the eGFP fluorescent signal in TNBC xenograft zebrafish was observed under fluorescent microscopy during a five-day continuous TP4 treatment (1 or 2 µg/mL).

FIG. 16 shows that TP4 enhanced immunogenicity in zebrafish embryos.

DETAILED DESCRIPTION OF THE INVENTION

Figure 1E:
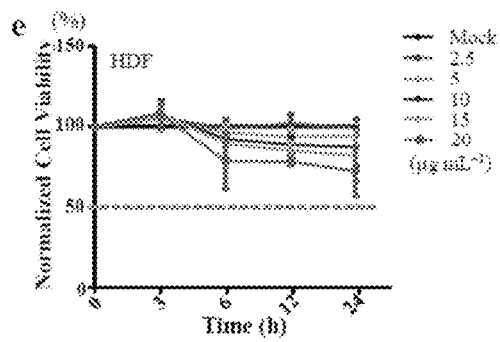

Unless defined otherwise, all technical and scientific terms used herein have the same meaning as commonly understood by a person skilled in the art to which this invention belongs.

As used herein, the singular forms "a", "an", and "the" include plural referents unless the context clearly dictates otherwise. Thus, for example, reference to "a sample" includes a plurality of such samples and equivalents thereof known to those skilled in the art.

As used herein, the term "tilapia piscidin 4" or "TP4" refers to a cationic antimicrobial peptide (CAP) or a functional fragment or variant thereof, which is derived from Nile Tilapia (*Oreochromis niloticus*). TP4 has the amino acid sequence of FIHHIIGGLFSAGKAIHRLIRRRRR (SEQ ID NO: 1), as disclosed in Peng et al. (Peng et al., Five different piscidins from Nile tilapia, *Oreochromis niloticus*: analysis of their expressions and biological functions; *PLoS One* 7(11):e50263, 2012).

The term "a functional fragment or variant thereof" as used herein refers to a fragment or variant of the peptide that maintains same or similar activity, and exhibits same or similar properties.

As used herein, "FBJ murine osteosarcoma viral oncogene homolog B," also known as "FOSB" or "FosB," refers to a protein that, in humans, is encoded by the FOSB gene. The FOSB gene belongs to one member of the FOS gene family, which encode leucine zipper proteins that can dimerize with proteins of the JUN family (e.g., c-Jun, JunD), thereby forming the transcription factor complex AP-1. As such, the FOS proteins have been implicated as regulators of cell proliferation, differentiation, and transformation.

It was unexpectedly found in the invention that a tilapia piscidin 4 (TP4) is potential for treatment of a cancer, through induction of FBJ murine osteosarcoma viral oncogene homolog B (FOSB).

In the invention, it is found that TP4 acts to control tumor cell growth by inducing an AP-1 protein called FOSB, the expression of which is negatively associated with the pathological grade of the tumor, and TP4 is targeted to the mitochondria where it disrupts calcium homeostasis and activates FOSB. FOSB overexpression results in TNBC cell death, whereas inhibition of calcium signaling eliminates FOSB induction and blocks TP4-induced TNBC cell death. Interestingly, both TP4 and anthracyclines strongly induced FOSB, particularly in TNBC, indicating that FOSB is suitable as a biomarker of drug responses. Accordingly, the invention provides TP4 can be used as a novel therapeutic approach toward a malignant tumor, such as TNBC, which involves targeting the "road-to-die" signaling mediated by FOSB.

In this invention, TP4 is found to be selectively toxic to breast cancer cells. According to the in vitro and in vivo data shown in breast cancer cell-lines and xenograft models as provided in the examples, it is indicated that TP4 can be developed as a novel agent to treat TNBC. It is found in the invention that TP4 damaged TNBC cells through the ERK/FOSB/cJUN axis in a calcium-dependent manner. Activation of FOSB in TNBC requires calcium signaling, which is transduced by selective targeting of TP4 to the mitochondria. In addition, induction of CDH1 by TP4 may also contribute to TNBC suppression. Interestingly, widely-used anthracyclines also induced FOSB in TNBC cells. This finding, together with the observation that FOSB overexpression triggers TNBC cell death, indicates that FOSB may be a novel therapeutic target for treating TNBC.

Figure 3F:
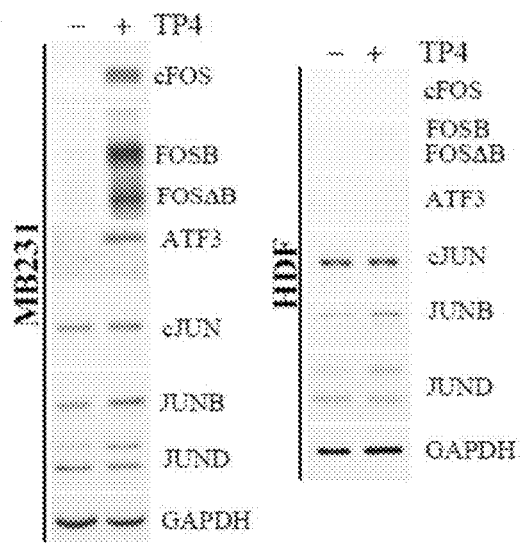
Figure 3G:
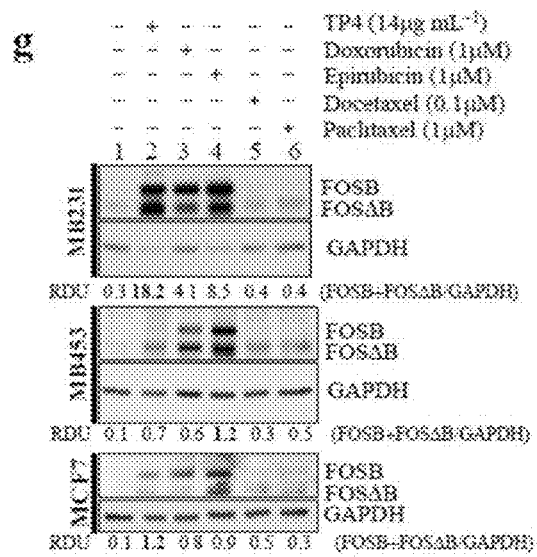
Figure 3H:
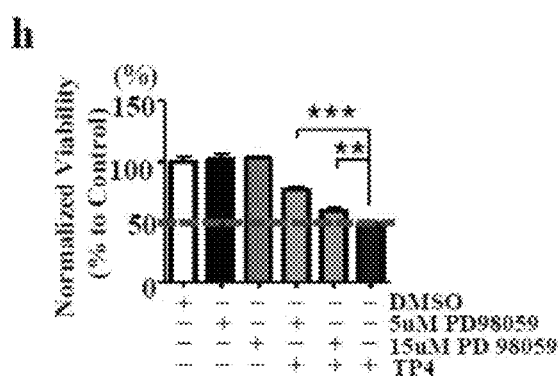
Figures 4A, 4B:
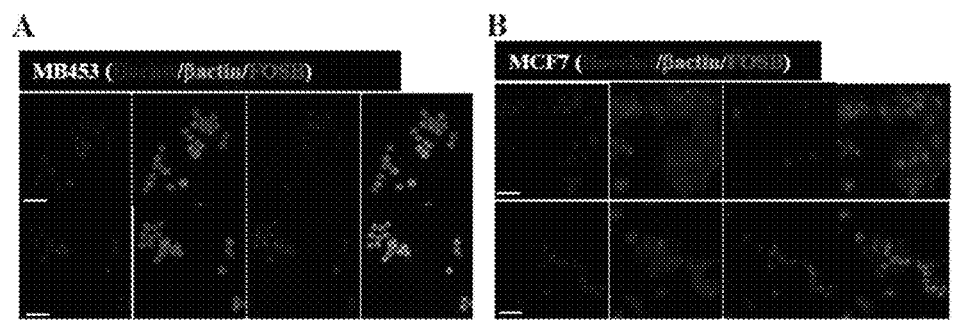
FIGS. 4A and 4B shows that TP4-(14 µg/mL) or mock-treated cells were stained with FOSB antibody (red) and β-actin (green) to show the induction of FOSB by TP4 in BC cells; wherein Hochest33342 dye was used for nuclear staining (blue). Bar: 50 µm.
Figures 4C, 4D:
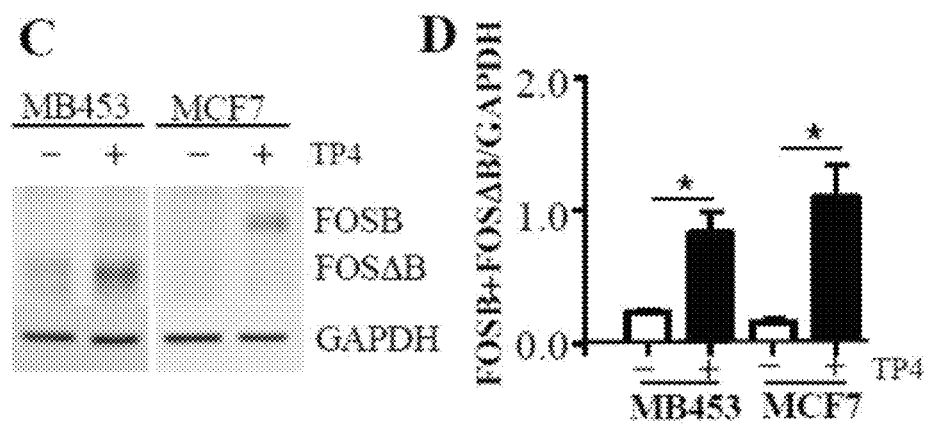
FIG. 4C shows total lysates from MB453 and MCF7 cells treated without (−) or with TP (+) were analyzed by Western blot using antibodies against GAPDH and FOSB.
FIG. 4D shows the results of the quantitative analysis of the blot shown in FIG. 4C using GAPDH as a control for normalization. Results represent the mean±SEM from three independent experiments performed in triplicate (Student's t-test: *, P<0.05).
Figure 6C:
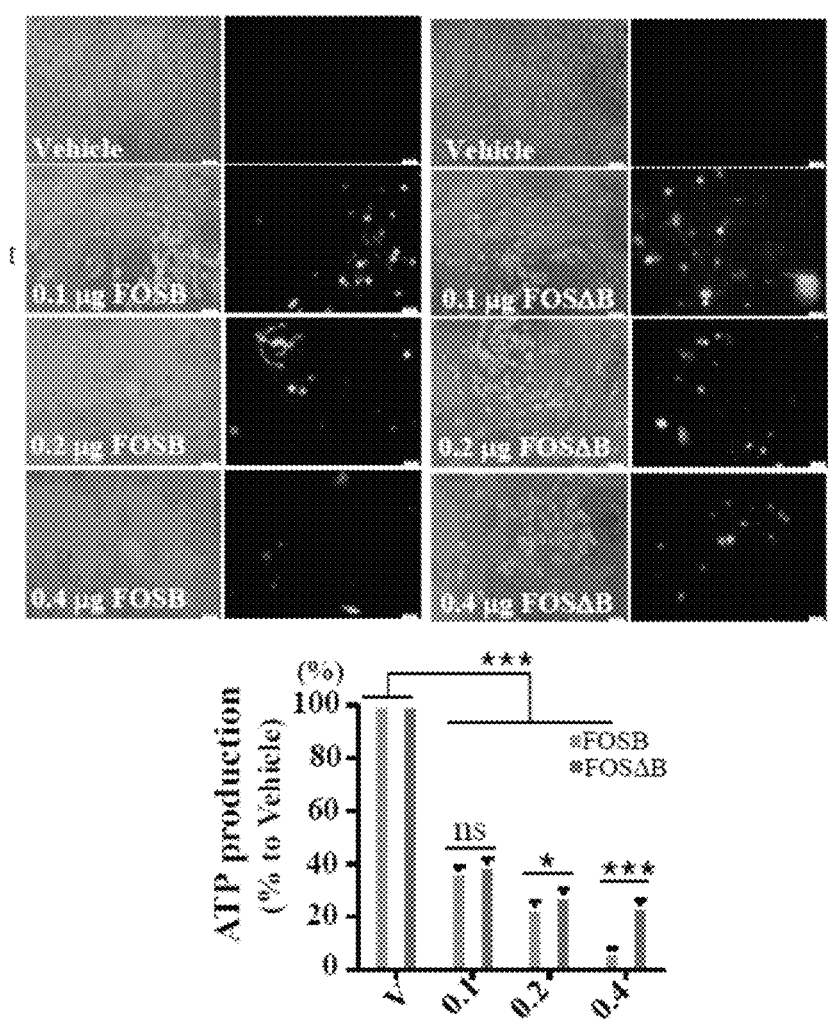
Figure 6D:
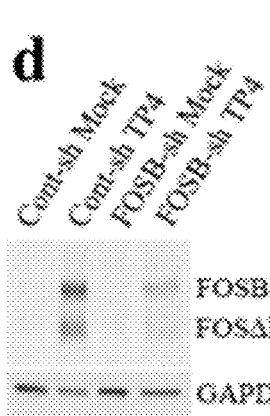
Figure 6E:
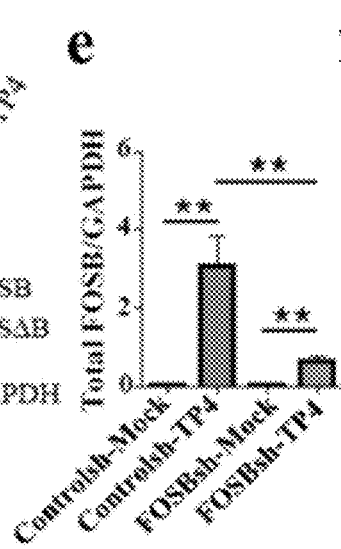
Figure 6F:
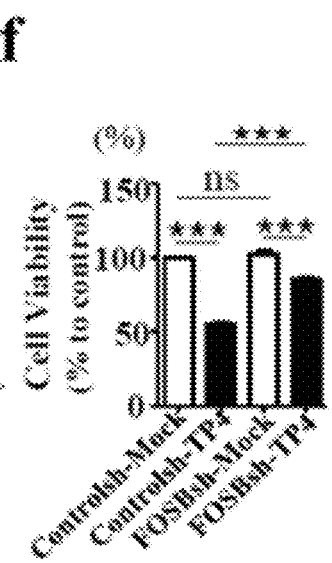
Figure 6G:
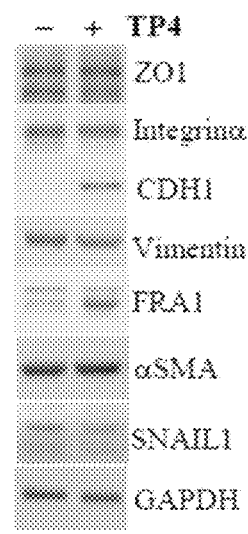
Figure 6H:
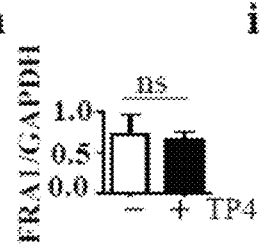
Figure 6I:
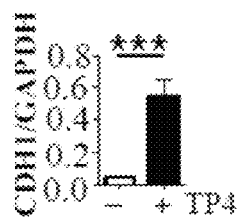
Figure 9I:
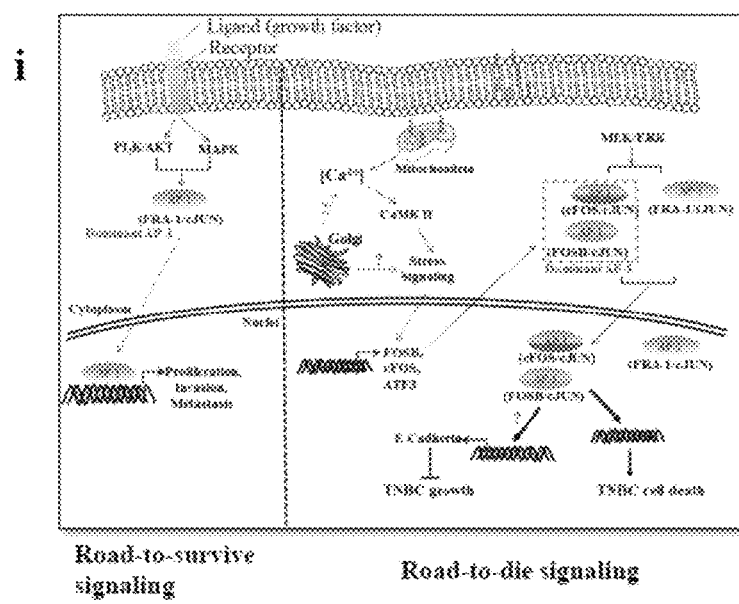

It is also found in the invention that the level of FOSB is significantly down regulated in grade II/III tumor samples (moderately differentiated or poorly differentiated tumor) isolated from TNBC patients (see FIG. 6a). It is also found that the level of FRA1 is not affected by TP4 in TNBC (FIGS. 6g, 6h). However, the expression of the tumor suppressor protein CDH1 (FIGS. 6g, 6i) is repressed by FRA-associated signaling, suggesting that the FRA1-mediated EMT program may have been disrupted by FOSB-induced changes in the dominant AP-1 complex in TNBC cells (FIG. 9i). Interestingly, FOSB exhibits differential patterns of post-transcriptional regulation among different subtypes of breast cancer. A greater proportion of full-length FOSB transcripts were found to be induced by TP4 or anthracyclines in MCF7 cells; conversely, less full length and but more FOSΔB transcripts were found in MB453 cells (FIG. 3g). Since overexpression of high concentrations of FOSAB is less toxic than FOSB overexpression to MB231 cells (FIG. 6(c)), it is possible that the FOSB, and not FOSAB, predominantly contributes to BC cell death. In support of this possibility, MB453 cell re-growth was observed at 12 h post-TP4 treatment, while MCF7 and MB231 cells did not regrow (FIGS. 1a-1c). It is indicated that FOSB may be a suitable biomarker for the response to anthracyclines in breast cancer cells. In addition, it was observed that the induction level of FOSB in TNBC cells is considerably higher than that in MCF7 and MB453 cells. It is not known whether hormonal or HER2 receptor status in different subtypes of breast cancer correlates with the efficacy of chemotherapy and the induction levels of biomarkers. Elucidation of cross-links between signaling pathways may facilitate greater understanding of drug resistance in different breast cancer subtypes.

Figure 1F:
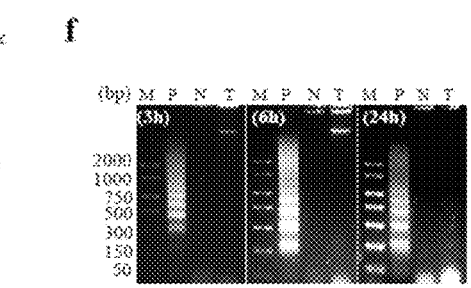
FIG. 1*f* shows the result of the detection of DNA fragmentation in TP4-treated MB231 cells by 2% agarose gel electrophoresis (Lane P: Positive control (Actinomycin D-treated HL60 cell lysate); lane N: Negative control (MB231 cell lysate); lane T: TP4-treated MB231 cell lysate; Lane M: DNA molecular weight marker.
Figure 1G:
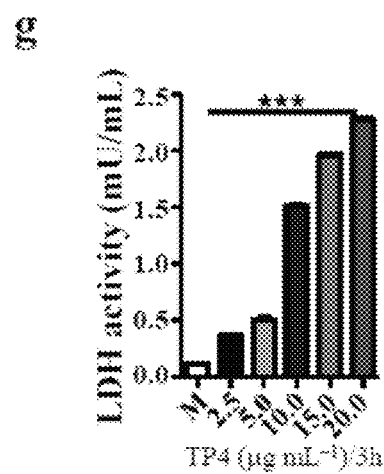
FIG. 1g shows the LDH levels in MB231 cells, which were determined after the treatment with different doses of TP4 (2.5-20 µg mL$^{-1}$) at 3 h. Sextuplicate wells were analyzed for each assay. Results represent the mean±SEM (n=3, One way ANOVA: ***, P<0.001 versus control, ns: not significant).

The mechanisms by which TP4 and anthracyclines induce FOSB and mediate BC cell death are different. While some BC-targeting peptides were reported to be localized to the nucleus and cause DNA fragmentation, no strong nuclei staining pattern of TP4 was observed in breast cancer cells (FIGS. 7a-7d), suggesting that TP4 may not influence the transcriptome in BC cells through the same manner as anthracyclines. In addition, doxorubicin was shown to cause an increase in mitochondrial calcium level in BC cells (Kuznetsov et al., Changes in mitochondrial redox state, membrane potential and calcium precede mitochondrial dysfunction in doxorubicin-induced cell death. *Biochimica et biophysica acta* 1813, 1144-1152, 2011), and trigger apoptotic cell death (Wang et al., Doxorubicin induces apoptosis in normal and tumor cells via distinctly different mechanisms. intermediacy of $H_2O_2$— and p53-dependent pathways. *The Journal of biological chemistry* 279, 25535-25543, 2004). TP4, however, caused calcium leakage from mitochondria (FIG. 9b), leading to necrosis (FIGS. 1e, 1g). Blockage of calcium signaling by the calcium chelator (BATPA-AM) eliminated FOSB induction and disrupted TP4-mediated TNBC cell death (FIGS. 9c-9e), indicating that FOSB may be useful as a specific biomarker of the response to TP4; however, here we did not examine whether FOSB induction by anthracyclines can also be blocked by treatment with a calcium chelator, and whether elimination of FOSB activation can disrupt anthracycline-induced BC cell death. Based on the finding that overexpression of FOSB triggered TNBC cell death (FIG. 6c), it can be concluded that FOSB activation may be useful as a response marker for testing cytotoxic agents against TNBC.

Figures 16A, 16B, 16C, 16D, 16E, 16F, 16G:
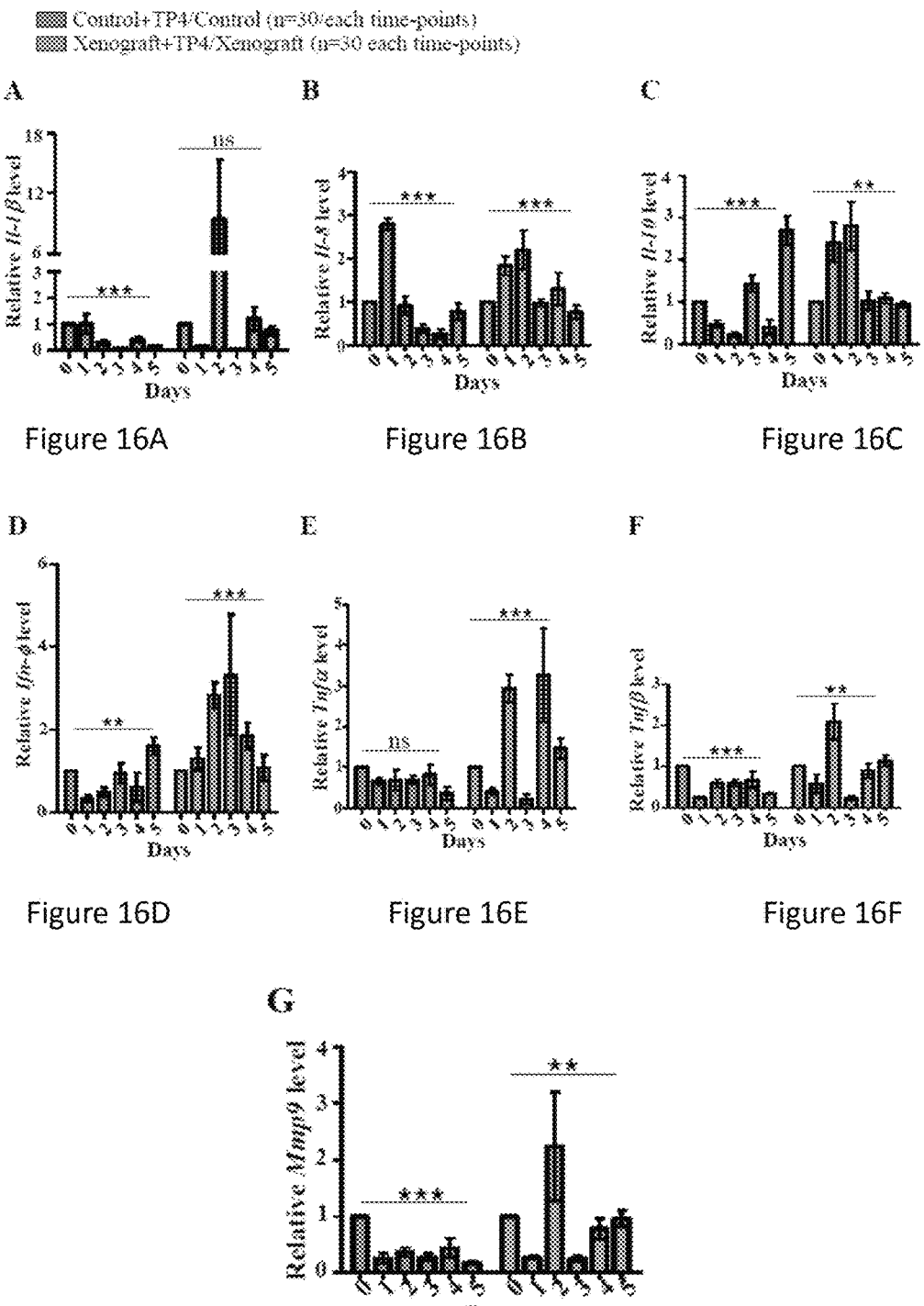
FIGS. 16(A)-16(G) show the real time PCR analyses of the relative immune gene expression profiles of control fish treated with and without TP4 or between TNBC xenograft fish treated with and without TP4. Statistical comparisons of immune genes between time-points were performed by one-way ANOVA analysis. ns: not significant; , P<0.01; *, P<0.001.

Intratumoral injection of TP4 caused extensive necrosis of TNBC in xenograft tumor (FIGS. 11d, 11e) without affecting body weight or causing adverse side-effects (FIG. 11c), suggesting that intratumoral injection of TP4 may be of practicable use for further therapeutic regimens. Another critical concern is that necrotic cell death caused by TP4 may trigger severe immunogenicity in vivo and further damage surrounding tissues. It is also observed that innate immunity was affected by TP4 treatment in both zebrafish embryos and TNBC xenograft embryos (FIG. 16). An enhancement of immune responsive gene expression was observed in TNBC xenograft embryos, particularly at days 1-3 (FIGS. 16A-16G, right). As TP4 did not appear to cause an overall induction of immune responses in normal embryos, we propose that the immunity may be enhanced by the self-defense mechanism against TNBC xenografts in zebrafish embryo. In the invention, non-TNBC cell autonomous effects in zebrafish embryo existed and helped eliminate cancer cells; however, the key players involved (e.g. neutrophils and macrophages) and the signaling pathway(s) required for their activation still need to be identified.

In summary, it can be indicated in the invention, (i) TP4 as a novel cytotoxic peptide possibly suitable for breast cancer therapy, and (ii) FOSB as a biomarker of the response to TP4 and anthracyclines, particularly in TNBC. In contrast to previous reports that TNBC can be suppressed through FRA1-mediated "road-to-survive" signaling inhibition, it is found in the invention that TNBC cell growth can be disrupted by FOSB up-regulation. TP4 and FOSB signaling are promising therapeutic candidates for TNBC treatment.

Accordingly, the invention provides a new approach using TP4 for treating a malignant tumor, a MDR cancer, a recurrent cancer or a metastatic cancer, wherein the cancer cells possess negatively-charged phosphatidylserine (PS) or anionic structures on their outer membrane.

Furthermore, the invention also provides a pharmaceutical composition for treating a subject with a malignant tumor, a MDR cancer, a recurrent cancer or a metastatic cancer, comprising a therapeutically effective amount of TP4 in combination with one or more anti-cancer drugs at a ratio to provide a synergistic effect in treating the cancer.

In the invention, the pharmaceutical composition may be formulated using any standard technology or commonly used methods known to those skilled in the art.

The term "therapeutically effective amount" as used herein refers to an amount of a drug or pharmaceutical agent which, as compared to a corresponding subject who has not received such amount, results in an effect in treatment or prevention of a disease, disorder, or side effect, or a decrease in the rate of advancement of a disease or disorder. The term also includes within its scope amounts effective to enhance normal physiological function.

For use in therapy, the therapeutically effective amount(s) of TP4 may be formulated as a pharmaceutical composition for administration.

Accordingly, the invention further provides a pharmaceutical composition comprising a therapeutically effective amount of TP4, together with one or more pharmaceutically acceptable carriers.

The term "a pharmaceutically acceptable carrier" as used herein refers to a carrier, diluent, or excipient that is pharmaceutically acceptable, in the sense of being compatible with the other ingredients of the formulation and not deleterious to the subject to be administered with the pharmaceutical composition. Any carrier, diluent or excipient commonly known or used in the field may be used in the invention, depending to the requirements of the pharmaceutical formulation.

According to the invention, the pharmaceutical composition may be adapted for administration by any appropriate route, including but not limited to topical, rectal, nasal, vaginal, oral or parenteral route. The present invention will now be described more specifically with reference to the following examples, which are provided for the purpose of demonstration rather than limitation.

EXAMPLES

1. Materials and Method
1.1 Reagents

TP4 (FIHHIIGGLFSAGKAIHRLIRRRRR, SEQ ID NO: 1) and TP4 biotinylated at the N-terminus were synthesized and purified by GL Biochem Ltd. (Shanghai, China) as previously described by Peng et al. Autocamtide-2 related inhibitory peptide II (AlP II) was purchased from EMD Millipore. BAPTA-AM [1,2-Bis(2-aminophenoxy)ethane-N,N,N,N-tetraacetic acid tetrakis(acetoxymethyl ester)], Paclitaxel, Docetaxel, Epirubicin hydrochloride, and Doxorubicin hydrochloride were purchased from Sigma.

1.2 Cell Culture and Stable Clone Selection

Cell-lines used in this study were purchased from the Bioresource Collection and Research Center (BCRC) in and the cells were cultured by the standard cell culture procedures and conditions provided by the BCRC. MB231 (BCRC 60425), MB453 (BCRC 60429), and HDF cells were cultured as previously described by Ting et al. MCF7 (BCRC 60429) cells were maintained in α-MEM medium (ThermoFisher Scientific) supplemented with 2 mM L-glutamine, 10% FBS, 0.1 mM non-essential amino acids, 1 mM sodium pyruvate, and antibiotics (100 U mL$^{-1}$ penicillin G and 100 g mL$^{-1}$ streptomycin). M10 (BCRC 60197) cells were maintained in α-MEM medium (ThermoFisher Scientific) supplemented with 10% FBS and antibiotics. With the exception of MB231 and MB453, all cells were cultured at 37° C. with 5% $CO_2$. For the cell viability and transfection assay, $1 \times 10^4$ cells [$5 \times 10^3$ M10 cells were seeded and cultured for 48 h to allow the cells sufficient time for attachment] were seeded into the wells of a 96-well plate and cultured overnight. For the transfection assays, cells were transfected with 0.1-0.4 μg FOSB/FOSAB expression plasmid (Origene Technology Inc.) and cell viability was determined after 72 h. The transfection efficiencies (number of cells expressing eGFP/all cells) of the MB231 transfection assays were determined by observing ten randomly selected fields (from three independent transfections) of control GFP plasmid transfections under an inverted microscope (Olympus, IX71) coupled to a digital camera (Olympus DP80), using an 10× objective lens (LCPlanFI 20×/0.40 Ph1). CellSens standard software (Olympus) was used for image acquisition. During the drug treatment assay, inhibitors (PD98059, BAPTA-AM, and AlP II) were added 30 min prior to TP4, and cell viability was determined at indicated time-points. Transfection was performed using LipofectAMINE™ 3000 (ThermoFisher Scientific), according to the manufacturer's recommendations. Knock-down cells were generated by transducing MB231 cells with pre-synthesized FOSB (or control) shRNA lentiviral particles (Santa Cruz Biotechnology), and selecting puromycin-resistant cells in accordance with the manufacturer's standard protocol. MB231 or M10 cells stably expressing eGFP or mOrange2 were generated through transfection with peGFP-puromycin or pmOrange2-C1 plasmid, followed by puromycin (5 μg mL$^{-1}$) or G418 (500 μg mL$^{-1}$) selection as described above.

1.3 Antibodies

Antibodies used in this study (for the results shown in the Supplementary Results) were as follows: β-actin (1:5000, clone AC-15) and caspase 3 (1:1000, clone 74T2) were from ThermoFisher Scientific; Cytochrome C (1:500, clone EP1326Y) was from EMD Millipore; cleavage-Caspase 3 (1:1000, clone 5A1E), SAPK/JNK (1:1000), phospho-SAPK/JNK (1:1000, clone 81E11), ERK1/2 (1:5000), and phospho-ERK1/2 (1:5000) were from Cell signaling; P38 MAPK and phospho-P38 MAPK were from BD Transduction Laboratories.

1.4 Cell Viability Assay

Cell viability was quantitatively analyzed using the CellTiter-Glo® Luminescent Cell Viability Assay kit (ATP assay) and CellTiter 96® AQueous Non-Radioactive Cell Proliferation Assay kit (MTS assay) (Promega) in accordance with the manufacturer's protocol. For MTS assay, $1 \times 10^4$ cells were seeded into the wells of a 96-well plate and cultured overnight [$5 \times 10^3$ M10 cells were seeded and cultured for 48 h to enable sufficient well attachment]. Cells were subsequently treated with different doses of TP4 (2.5-20 μg mL$^{-1}$) and harvested at the indicated time-points (3-24 h). Reaction mixtures (20 μL: MTS+PMS, using a ratio 20:1) were directly added to the cells, and the plates were incubated for 3 h at 37° C. Absorbance at 490 nm is directly proportional to the number of living cells in culture and was measured using a photometer (SpectraMax® i3, Molecular Devices). ATP assay was performed as previously described by Ting et al. Lactate dehydrogenase (LDH) assays were performed by quantitatively measuring cell lysis with a Cytotoxicity Detection Kit$^{PLUS}$ (LDH) (Roche) in accordance with the manufacturer's protocol. The LDH standard was purchased from Cayman Chemical. Briefly, $1 \times 10^4$ cells were seeded into the wells of a 96-well plate and cultured overnight. Culture media were replaced with fresh medium containing 1% FBS and cells were subsequently treated with different doses of TP4 (2.5-20 μg mL$^{-1}$). Supernatants were harvested at 3 h. After centrifugation at 200×g for 5 min to remove cell debris, supernatants were collected and 50 μL were aliquoted from each well into a new microplate. Reaction mixtures were then added and incubated for 15 min at RT. Stop solution was added to the well, and absorbance at 490 nm was determined with a reference wavelength of 600 nm.

1.5 DNA Laddering Assay

DNA fragmentation was analyzed using the SuicideTrack™ DNA Ladder Isolation Kit (EMD Millipore) in accordance with the manufacturer's standard procedures. Sufficient DNA samples from TP4 treatment groups were extracted by collecting cells from ten 10 cm$^2$ dishes. Precipitated DNA samples were analyzed by 1.5× agarose gel electrophoresis.

1.6 Transcriptome Analysis

Total RNA samples were extracted from MB231 and HDF cells treated with TP4 (14 μg/mL) for 6 h. Total RNA (0.2 μg) was amplified using a Low Input Quick-Amp Labeling kit (Agilent Technologies, USA), and the cDNA was labeled with Cy3 (CyDye, Agilent Technologies, USA) during the in vitro transcription process. Cy3-labeled cRNA (0.6 μg) was fragmented to an average size of about 50-100 nucleotides by incubation with fragmentation buffer at 60° C. for 30 min. Corresponding fragmented labeled cRNA was then pooled and hybridized to an Agilent SurePrint G3 Human V2 GE 8×60K Microarray (Agilent Technologies, USA) at 65° C.

for 17 h. After washing and drying using a nitrogen gun blowing, microarrays were scanned with an Agilent microarray scanner at 535 nm to detect Cy3. Scanned images were analyzed using Feature extraction 10.5.1.1 software (Agilent Technologies, USA); image analysis and normalization software was used to quantify signal and background intensity for each feature.

1.7 AP-1 Transcription Factor Activation Assay

Activation of AP-1 was determined using the TransAM AP-1 kit (Active Motif, Inc), as previously described by Ting et al.

1.8 Coimmunoprecipitation and Western Blot

Nuclear extracts were prepared as previously described[23]. Equal amounts of nuclear extract (200 µg) were used for immunoprecipitation (IP) using Dynabeads protein G (ThermoFisher Scientific), in accordance with the recommended protocol. cJUN antibody (ThermoFisher Scientific, clone C.238.2) was used for immunoprecipitation. Total cell extract preparation and Western blot were performed as previously described[23]. Equal amounts of boiled lysate (20 µg of total cell extract) were separated on acrylamide gels, and then transferred to PVDF membranes. The membranes were incubated in blocking solution (0.1 M PBS, 5% non-fat milk, 0.2% Tween-20) for 1 h at room temperature (RT), and then incubated in the same solution with primary or secondary antibodies (GE Healthcare Life Science). Primary antibodies were as follows: c-FOS (Cell signaling, 9F6, 1:1000), FOSB (Cell Signaling, 5G4, 1:1000), FRA1 (Cell Signaling, D80B), ATF3 (EMD Millipore, 6B8, 1:500), JUNB (Cell Signaling, C37F9, 1:1000), JUND (EMD Millipore, 1:1000), c-JUN (EMD Millipore, 6A6.2, 1:2000), Vimentin (Abcam, EPR3776, 1:5000), CDH1 (Cell Signaling, 24E10, 1:1000), Integrin α5 (Cell Signaling, 1:1000), Glyceraldehyde-3-phosphate dehydrogenase (GAPDH, EMD Millipore, clone 6C5, 1:10,000), αActin (smooth muscle) (αSMA, OriGene Technologies, 1:5,000), SNAI1 (ABGENT, N-term D24, 1:500), and ZO1 (ThermoFisher Scientific, 1:1,000). Membranes were visualized with enhanced chemiluminescence (Immobilon Western Chemiluminescent HRP substrate, Merck Millipore) and detected by an imaging system (UVP, BioSpectrum™ 500). Signal intensities were determined by densitometric analysis (AlphaInnotech) using the AlphaImager program. The results were expressed as relative densitometric units (RDU) (the densitometric units of FOSB+FOSΔB divided by those of GAPDH).

1.9 Calcium Measurement

Calcium ($Ca^{2+}$) levels were determined using the Fluo-4 acetoxymethyl ester (AM) Direct $Ca^{2+}$ assay kit (ThermoFisher Scientific) and Rhod-2 calcium indicator (ThermoFisher Scientific), as recommended by the manufacturer. Briefly, $1\times10^4$ cells were seeded into a well of a 96-well plate and cultured overnight. Eight replicates were performed for each condition. Cytosolic calcium was measured by adding 2× Fluo-4 Direct™ reagent (final probenecid concentration of 5 mM) directly to each well, and then incubating the plates for 30 min at 37° C., and subsequently for 30 min at RT. Cells were treated with TP4 (5-20 µg $mL^{-1}$) for 5, 10, 20, or 30 min. Fluorescence was subsequently measured using a fluorescence reader (SpectraMax® i3, Molecular Devices), using instrument settings appropriate for excitation at 494 nm and emission at 516 nm. $Ca^{2+}$ levels are presented as relative fluorescent units (ΔRFU), determined using the following equation: $F-F_{min}/F_{min}$, where $F_{min}$ denotes the background-subtracted pre-stimulus fluorescence level. Mitochondrial $Ca^{2+}$, was measured by incubating cells with 2 µM Rhod-2 AM ester and 0.02% pluronic F-127 for 30 min at 37° C. After three washes in D-PBS, cells were incubated for 30 min in culture medium at 37° C. Cells were treated with TP4 (5-20 µg $mL^{-1}$) and fluorescence was determined kinetically every 30 sec for 30 min using a fluorescence reader with instrument settings appropriate for excitation at 552 nm and emission at 581 nm. Mitochondrial $Ca^{2+}$ levels are presented as relative fluorescent units F/F0, where F0 denotes the un-stimulated fluorescence level.

1.10 Immunocytochemical, Immunohistochemical, and Whole-Mount Studies

The plasma membrane and mitochondria were stained by pre-incubating biotinylated-TP4 treated cells (14 µg $mL^{-1}$, 3 h) with Alexa Flour 647 dye-conjugated wheat germ agglutinin (WGA) (5 µg $mL^{-1}$) (ThermoFisher Scientific) for 10 min at 37° C. or with MitoTracker® Red CMXRos probe (200 nM) (ThermoFisher Scientific) for 45 min at 37° C. prior to cell fixation. Cells were then fixed with 4% PFA (in PBS) for 15 min, and permeabilized with 0.1% Triton X-100 in PBS (PBST) for 12 min at RT. After blocking with 5% BSA in PBST, the cells were incubated overnight at 4° C. with Biotin (Santa Cruz Biotechnology, 39-15D9, 1:500), Calreticulin (1:500), Giantin (Abcam, 1:1000), or FOSB (1:500) antibody. Cells were then washed three times with TBS-T (20 mM Tris-HCl, pH 7.4, 137 mM NaCl, and 0.1% Tween-20), and incubated for 1 h at RT with secondary antibodies (1:500; ThermoFisher Scientific) conjugated to the appropriate fluorescent dye. Hochest33342 was used for nuclear staining. The fluorescent signal (which is proportional to functional mitochondria) was quantitatively determined using Image J software. Human breast adjacent normal tissue array (BRN801a) and TNBC tissue array (BR487a) were purchased from US Biomax, Inc. Commercially-available human tissue samples were used in accordance with the regulations of the "Human Subject Research Ethics Committee" of Academia Sinica. Paraffin sections were immunostained with FOSB antibody (1:50) and Hochest 33342. Fluorescent images were obtained with an inverted microscope (Olympus, IX71) coupled to a digital camera (Olympus DP80), using a 4× (UPlanFI 4×/0.13 PhL) objective lens. CellSens standard software (Olympus) was used for image acquisition. The fluorescent FOSB signal was quantitatively determined using Image J software. For whole mount staining, xenograft zebrafish were fixed using 4% PFA for 1 h at RT. After four washes for 5 min each in PBST (1% Triton-X-100), fish were incubated in blocking buffer (PBS+1% triton-X-100+10% FBS) for 1 h at RT. Fish were then washed twice with blocking buffer and incubated with FOSB antibody (1:50) for 2 days in blocking buffer. After a further three washes for 1 h each in PBST, fish were incubated with secondary antibody conjugated to Alexa Flour 647 for 2 h at RT. Fish were then washed three times with PBST for 10 min each at RT. After mounting (tissues or cells) with fluorescent mounting medium (ProLong Gold Antifade Reagent, ThermoFisher Scientific), images were obtained with an FV1000 laser-scanning confocal microscope (Olympus), using a 10× (Olympus UPlanSApo 10×, N.A. 0.40) or 60× objective lens (Olympus UPlanSApo 60×, N.A. 1.35, oil). ASW2.1 software (Olympus) was used for image acquisition, disseminated tumor foci quantitation, and the measurement of primary tumor area.

1.11 Mice and Pathological Studies

Female BALB/c nu/nu mice were obtained from BioLASCO Taiwan, Co., Ltd., and housed at the Laboratory Animal Facility, National Taiwan Ocean University, Keelung, Taiwan. Mice were maintained in pathogen-free sterile isolators, according to the guidelines of the Council of Agriculture (COA, Taiwan), and all food, water, caging, and bedding were sterilized before use. The animal protocol (103034) was approved by the Institutional Animal Care and Use Committee (IACUC) of the College of Life Science, National Taiwan Ocean University. For the TP4 treatment assay, nude mice with pre-growth MB231 tumors (n=5 for each group) were subcutaneously injected with TP4 (500 μg in 50 μL distilled water plus 10 μL KY jelly (Johnson & Johnson)) every two days for a total of fourteen times, by which time the tumors had reached an average volume of 30-50 $mm^3$ in size. Age-matched control nude mice without tumor xenografts were injected with KY jelly (10 μL plus 50 μL distilled water). Tumor size was calculated every two days, using the following formula: volume=[(height×length×width)×3.1416]/6. Mice were sacrificed 28 days after the beginning of TP4 treatment, and the tumors were harvested and weighed. Tumor samples were fixed with formalin and embedded with paraffin. Paraffin sections were stained by Hematoxylin & Eosin (H&E) and immunostained with Ki-67 antibody (Cell Signaling, clone D2H10, 1:100). Images were obtained with an inverted microscope (Olympus, IX71) coupled to a digital camera (Olympus DP80), using a 10× (UPlanFI 10×/0.30 Ph1) and 40× (LUCPlanFI 40×/0.60 Ph2) objective lens. CellSens standard software was used for image acquisition. Fluorescent images were obtained with an FV1000 laser-scanning confocal microscope, using a 10× objective lens (UPlanSApo 10×, N.A. 0.40). ASW2.1 software was used for image acquisition and analysis.

1.12 Zebrafish Xenotransplantation Model

AB line zebrafish (*Danio rerio*) were provided by the Taiwan Zebrafish Core Facility (Academia Sinica). The transgenic line (fli:eGFP) was a kind gift from JY LIN Trading Co., Ltd (Pingtung, Taiwan). Fish care, maintenance, and experimental procedures were performed in accordance with "The Ethical Guideline for Using Vertebrates as Experimental Animals in Taiwan", and were approved by the "Ethical Committee for Using Vertebrates as Experimental Animals" of Academia Sinica. Tumor cell xenotransplantation protocols were performed in accordance with previously published methods with modifications[44,45]. Briefly, fertilized zebrafish eggs were incubated at 28° C. in E3 embryo medium (5 mM NaCl, 0.17 mM KCl, 0.33 mM $MgSO_4$) containing 0.2 mM PTU (Sigma). After de-chorionization at 24 hpf (hour-post-fertilization), eggs were soaked in E3 medium with tricaine (0.02 mg/mL, Sigma). After 24 h (48 hpf), embryos were orientated on a 1.8% agarose-modified microinjection plate. Tumor cells ($2 \times 10^6$ of MB231 or M10 cells expressing eGFP/mOrange2) were suspended in 25 μL Matrigel® matrix (12.0 mg $mL^{-1}$) solution (Corning), and 10-15 nL cell suspensions were microinjected into embryos (parameters were set at 7.0 psi and 0.5-1.0 secs). Xenografted embryos were placed in a 96 well black plate with a clear bottom (Coring) and then immobilized with methyl cellulose (1.25 μL); images were obtained with an inverted microscope (Olympus IX71) equipped with a camera (Olympus DP80), using a 4× objective lens (Olympus UPlanFI 4×/0.13 phL). On every subsequent day for 5 days, the media in each well were replaced with fresh E3 media containing TP4 (3 μg $mL^{-1}$), and images were obtained. The fluorescent signal (which is proportional to the number of eGFP-expressing cells) was quantitatively determined using Image J software. For time-lapse studies, immobilized and xenograft embryos received a single dose of TP4 or mock treatment before imaging and were incubated at 28° C. for 48 h. Images were obtained using the ImageXpress Micro HCS Image System (Molecular Devices). Images (including z stacks) were recorded under a 4× objective lens (Plan Fluor 4×/0.13) at 1 h intervals, using transmitted light and the FITC (EX 482/35, EM 536/40) and TRITC (EX 543/22, EM 593/40) filter sets. Every channel was captured from 5 images along the z-axis across a distance of 70 μm, and was composited to the best-focus image. Images were taken and tumor analysis was performed using the integrated MetaXpress® program (v.5.3, Custom Module Editor) to quantify the area and fluorescence intensity of the tumor inside the zebrafish. Normalized data are expressed relative to the value at 0 h.

1.13 TUNEL Staining

TUNEL (TdT-mediated dUTP nick end labeling) staining was performed using the In Situ Cell Death Detection Kit, POD (Roche) following the standard procedures recommended by the manufacturer. Briefly, cells (MB231 and HDF) were seeded onto the chamber slide and incubated overnight. Cells were blocked, fixed, and permeabilized after TP4 treatment for 3 or 6 h. The labeling solution and TUNEL reaction mixture were then added to the cells. After three washes in PBS, cells were subjected to nuclear staining by Hochest33342. Cell images were subsequently acquired using the FLoid cell imaging station (ThermoFisher Scientific). Cells treated with DNase I served as a positive control and cells untreated with terminal transferase (the enzyme mixture) served as negative control.

1.15 Quantitative Real-Time PCR

Zebrafish were collected (n=10 per group, for 3 experiments, a total of 30 zebrafish) at days 1-5 and homogenized in 300 μL Qiazol (Qiagen). Homogenates were vortexed for 15 sec, left to stand at RT for 5 min, and then added to 60 μL of chloroform. The mixtures were then vortexed for 15 sec, left to stand at RT for a further 3 min, and then transferred to the Phase Lock Gel™ (5 PRIME). After centrifugation at 12,000×g for 15 min, the supernatants were collected and processed using the RNA extraction kit (WELGENE Biotech). For reverse transcription, 1 μg of total RNA and the ProtoScript® II First Strand cDNA Synthesis Kit (New England Biolabs) were used by following the manufacturer's recommendations. For real-time PCR, 1.5 μL cDNA and SYBR Green Real-time PCR Master Mix (TOYOBO) were used with the StepOnePlus Real-Time PCR System (Applied Biosystems, Life technologies). The PCR condition was as follows: 95° C. for 1 min (holding stage); 40 cycles of 95° C. for 15 sec, 60° C. for 15 sec, and 72° C. for 45 sec; 95° C. for 15 sec, 60° C. for 1 min, and 95° C. for 15 sec (Melting curve stage). To analyze gene expression, the ΔΔCT method was performed with α-tubulin (Tub-α1b) as the calibrator gene. Primer sequences were as follows:

```
Tubα1b:
                                       (SEQ ID NO: 2)
    F: TTCCCTCTGGCTACCTATG;

(SEQ ID NO: 3)
    R: TCTTGATGGTGGCGATTGCG;

Cxcl8a:
                                       (SEQ ID NO: 4)
    F: CTCACTTAGGCAAAATGACCAG;

(SEQ ID NO: 5)
    R: TTCCAATGCGTCGGCTTTC;

Ifnϕ:
                                       (SEQ ID NO: 6)
    F: GCCGATACAGGATAATAACGACAG;
```

-continued

R: AGTGTTTTGGTCCCAGTT; (SEQ ID NO: 7)

Il1β:

F: TTTGTGGGAGACAGACGGT; (SEQ ID NO: 8)

R: CCAACTGCTTCATTTTGTGC; (SEQ ID NO: 9)

Il10:

F: AGCACTCCACAACCCCAATC; (SEQ ID NO: 10)

R: GACCCCCTTTTCCTTCATC; (SEQ ID NO: 11)

Mmp9:

F: CATCCGCAACTACAAGAC; (SEQ ID NO: 12)

R: TCACCTGGAGGATAAGCG; (SEQ ID NO: 13)

Tnfα:

F: TCTTCAAAGTCGGGTGTATG; (SEQ ID NO: 14)

R: GGTCATCTCTCCAGTCTAAGG; (SEQ ID NO: 15)

Tnfβ:

F: GCCAAACGAAGAAGGTCAG; (SEQ ID NO: 16)

R: CACCGCCAACCCATTTCA. (SEQ ID NO: 17)

1.16 Statistical Analysis

For the multi-well based assay, cells were plated at least in sextuplicate. Data were collected from independently repeated experiments (n 3) and were analyzed by Prism 5 software (GraphPad Inc.). The statistical significance of any difference was determined by applying the two-tailed t-test or one-way/two-way analysis of variance (ANOVA) with Bonferroni post-test. The difference was considered statistically significant at $P<0.05$.

2. Results 2.1 TP4 Induces Selective Necrosis of TNBC Cells

Different molecular subtypes of BC cell-lines (MDA-MB231, MDA-MB453, and MCF7) were subjected to the MTS assay to investigate whether TP4 can selectively kill BC cells in vitro. It was observed that treatment with 15 μg mL$^{-1}$, 5.03 μM of TP4 is sufficient to kill over 50% BC cells at 6 h, while the same dose had only minor effects on the viability of control normal human mammary epithelial cells (M10) or dermal fibroblasts (HDFs) (FIGS. 1a-1e and Table 1). Genomic DNA samples from TP4-treated MDA-MB231 cells (denoted as MB231) were taken at different time-points and subjected to a DNA laddering assay; no obvious DNA fragmentation was observed after TP4 treatment, indicating that TP4 does not induce apoptosis in TNBC cells (FIG. 1f). In addition, TUNEL staining of TP4-treated MB231 or HDF cells revealed very limited DNA fragmentation (FIGS. 2A, 2B) and no obvious caspase3 activation was observed in TP4-treated TNBC cells (FIGS. 2C, 2D). On the other hand, a necrotic marker, lactate dehydrogenase (LDH), was significantly increased at 3 h post-TP4 treatment in TNBC cells, and this increase was dependent on dose (FIG. 1g). Given the above, the findings indicated that TP4 induced necrotic death in TNBC cells. Statistical results from FIGS. 1a-e are shown. Sextuplicate wells were analyzed for each experiment (n=18 per dose). Results represent the mean±SD from three independent experiments. Statistical comparisons between mock versus TP4 treatment groups were performed using Two-way ANOVA analysis with Bonferroni post-hoc test: a, not significant; b, $P<0.05$; c, $P<0.01$; d, $P<0.001$.

TABLE 1

Cellular toxicity of TP4 to cells evaluated by MTS assay

| | | Dose (μg/mL) | | | |
|---|---|---|---|---|---|
| Time | 2.5 | 5.0 | 10.0 | 15.0 | 20.0 |
| | | MB231 | | | |
| 3 h | 95.34 ± 5.56[a] | 90.55 ± 10.57[a] | 75.01 ± 11.29[d] | 52.48 ± 11.16[d] | 30.57 ± 4.64[d] |
| 6 h | 95.93 ± 8.86[a] | 82.30 ± 6.40[d] | 65.28 ± 6.61[d] | 42.59 ± 10.14[d] | 26.65 ± 7.16[d] |
| 12 h | 87.60 ± 12.28[c] | 79.00 ± 9.48[d] | 61.63 ± 11.38[d] | 38.31 ± 7.26[d] | 19.31 ± 5.73[d] |
| 24 h | 87.01 ± 9.69[c] | 71.69 ± 6.84[d] | 57.98 ± 6.62[d] | 29.78 ± 4.79[d] | 16.19 ± 4.15[d] |
| | | MB453 | | | |
| 3 h | 93.75 ± 4.33[d] | 91.50 ± 4.32[d] | 77.82 ± 4.33[d] | 53.12 ± 10.90[d] | 36.33 ± 5067[d] |
| 6 h | 86.51 ± 4.19[d] | 76.46 ± 6.25[d] | 58.58 ± 5.43[d] | 27.09 ± 2.54[d] | 18.25 ± 1.80[d] |
| 12 h | 92.21 ± 6.61[d] | 80.18 ± 5.41[d] | 62.25 ± 10.74[d] | 27.32 ± 5.51[d] | 15.02 ± 4.28[d] |
| 24 h | 87.84 ± 4.75[d] | 87.00 ± 4.16[d] | 77.24 ± 4.07[d] | 58.93 ± 2.80[d] | 40.15 ± 2.66[d] |
| | | MCF7 | | | |
| 3 h | 98.00 ± 6.05[a] | 83.74 ± 6.10[d] | 75.01 ± 11.15[d] | 45.15 ± 9.89[d] | 24.63 ± 3.80[d] |
| 6 h | 91.20 ± 6.51[b] | 79.17 ± 12.06[d] | 70.30 ± 12.26[d] | 28.28 ± 6.29[d] | 15.48 ± 2.33[d] |
| 12 h | 93.01 ± 10.60[b] | 77.79 ± 7.73[d] | 68.89 ± 6.54[d] | 26.23 ± 6.08[d] | 14.36 ± 2.10[d] |
| 24 h | 90.83 ± 5.30[b] | 75.19 ± 11.28[d] | 67.00 ± 10.90[d] | 25.09 ± 3.83[d] | 11.90 ± 3.39[d] |
| | | M10 | | | |
| 3 h | 100.77 ± 4.23[a] | 97.11 ± 4.90[a] | 90.78 ± 4.76[d] | 84.85 ± 5.83[d] | 67.92 ± 5.16[d] |
| 6 h | 94.75 ± 7.52[c] | 92.00 ± 5.12[d] | 83.95 ± 7.47[d] | 78.87 ± 5.57[d] | 60.27 ± 4.97[d] |
| 12 h | 96.05 ± 5.66[a] | 92.62 ± 4.99[d] | 83.77 ± 4.27[d] | 65.49 ± 6.68[d] | 47.16 ± 8.42[d] |
| 24 h | 93.97 ± 3.81[d] | 91.22 ± 3.99[d] | 80.69 ± 5.72[d] | 58.41 ± 6.80[d] | 44.02 ± 4.50[d] |

TABLE 1-continued

Cellular toxicity of TP4 to cells evaluated by MTS assay

| | Dose (μg/mL) | | | | |
|---|---|---|---|---|---|
| Time | 2.5 | 5.0 | 10.0 | 15.0 | 20.0 |
| | | | HDF | | |
| 3 h | 105.05 ± 6.49$^a$ | 103.37 ± 5.88$^a$ | 101.86 ± 9.49$^1$ | 102.67 ± 9027$^a$ | 98.64 ± 12.96$^a$ |
| 6 h | 98.59 ± 4.42$^a$ | 96.79 ± 3.43$^a$ | 92.87 ± 2.98$^c$ | 90.85 ± 6.82$^d$ | 80.98 ± 12.27$^d$ |
| 12 h | 100.01 ± 4.74$^a$ | 93.79 ± 3.81$^b$ | 89.56 ± 3.87$^d$ | 85.92 ± 4.24$^d$ | 80.46 ± 1.58$^d$ |
| 24 h | 97.20 ± 5.62$^a$ | 92.72 ± 6.58$^c$ | 86.10 ± 9.39$^d$ | 82.22 ± 11.37$^d$ | 72.18 ± 13.50$^d$ |

2.2 FOS Family Members were Induced by TP4 in TNBC Cells

To characterize the downstream events which contribute to TP4-induced TNBC death, we analyzed gene expression profiles through microarray studies. Gene ontology (GO) analysis revealed that TP4 treatment caused dramatic changes in the gene expression profiles of TNBC cells (FIGS. 3a and 3b), but minor changes in HDF cells (FIG. 3b). Of note, FOS members (FOSB, c-FOS) and ATF3 were significantly induced in TNBC cells (FIG. 3b). Immunocytochemical studies and Western blotting confirmed that FOS members, and FOSB in particular, were induced, in tested BC cell-lines (FIGS. 3c-3h and FIGS. 4A-4D). With the exception of JUNB, JUN family proteins were not significantly affected in TNBC cells (FIGS. 3d, 3e). Neither FOS nor JUN family members were significantly affected in control HDF cells (FIGS. 3d, 3f). To explore the therapeutic role of FOSB, we investigated whether FOSB induction could be observed in TNBC cells during treatment with anthracycline or taxane-based chemotherapeutic agents. Interestingly, anthracyclines (doxorubicin and epirubicin) (FIG. 3g, lanes 3 and 4) induced strong FOSB expression, comparable to that induced by TP4 treatment of TNBC cells (FIG. 3g, lane 2). Taxane-based agents (docetaxel and paclitaxel), however, induced FOSB in MDA-MB453 (denoted as MB453) and MCF7 cells, but not in MB231 cells (FIG. 3g, lanes 5 and 6). These findings suggest that TP4 and anthracyclines act through a similar therapeutic pathway in TNBC cells. In addition, Kyoto Encyclopedia of Genes and Genomes (KEGG) analysis of the microarray data revealed a significant effect of TP4 treatment on MAPK signaling (Table 2); this signaling pathway is known to regulate AP-1 activity (Karin; The regulation of AP-1 activity by mitogen-activated protein kinases. *The Journal of biological chemistry* 270, 16483-16486, 1995).

TABLE 2

KEGG categories of pathways significantly affected by TP4 treatment of MB231 cells.

| Description | Term | Count | P-Value |
|---|---|---|---|
| MAPK signaling pathway | hsa04010 | 14 | 8.46E−03 |
| Adherens junction | hsa04520 | 6 | 3.25E−02 |
| Circadian rhythm | hsa04710 | 3 | 3.52E−02 |
| p53 signaling pathway | hsa04115 | 5 | 7.22E−02 |
| Pathways in cancer | hsa05200 | 13 | 7.66E−02 |

Figure 5A:
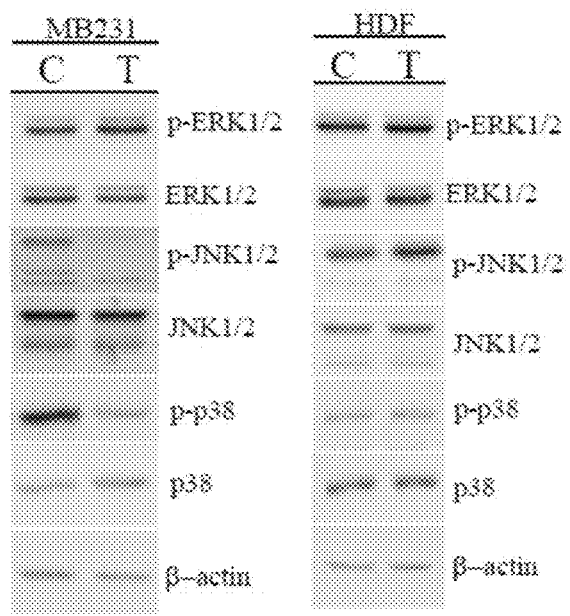
FIGS. 5A-5C show that MAPK pathways were affected by TP4 in MB231 cells.
Figure 5B:
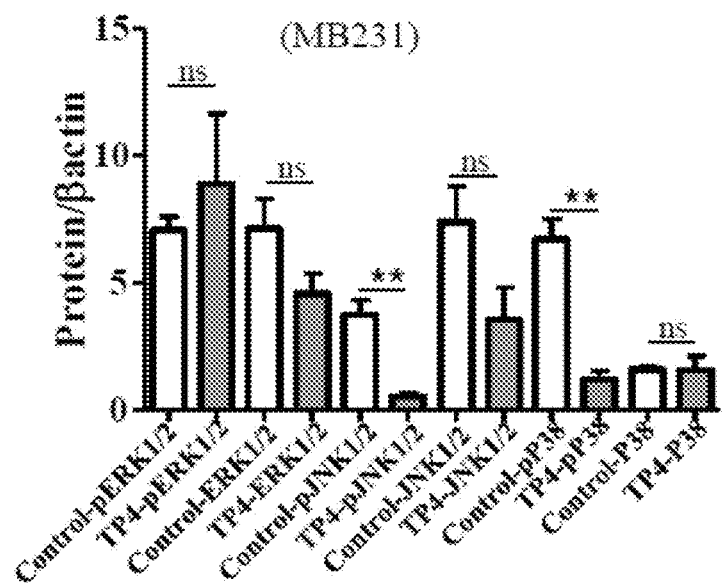
Figure 5C:
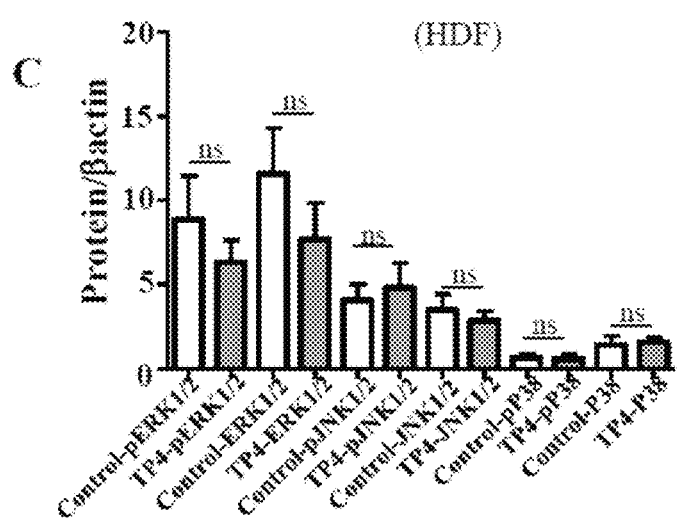

The molecules involved by Western blotting were further examined. It was observed that active forms of both JNK and p38 were significantly decreased by TP4 treatment in TNBC cells, but not in control HDF cells (FIGS. 5(A)-5(C)). Activation of ERK proteins had no significant effect (FIGS. 5A, 5B), but inhibition of ERK activity by PD98059 disrupted TP4-induced TNBC cell death, as shown by MTS assay (FIG. 3h); these findings suggest that ERK signaling is required for TP4-mediated cell death.

2.3 TP4 Induces FOSB to Trigger TNBC Cell Death

Figure 6J:
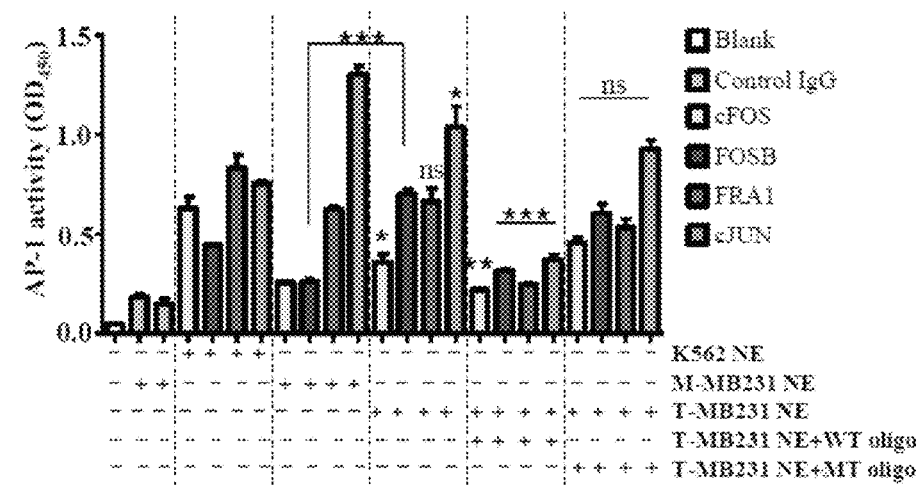

Strong induction of FOSB by TP4 in TNBC cells suggested possible involvement of FOSB in TP4-mediated TNBC cell death. A previous study indicated that FOSB is highly expressed in normal ductal mammary epithelium, but not in poorly differentiated ductal carcinoma[40]. To address whether FOSB expression is associated with TNBC progression, we analyzed FOSB expression in various grades of tumor samples from TNBC patients by immunohistochemical analysis. Expression of FOSB in breast normal adjacent tissue (NAT, n=26) was found to be stronger than expression in grade II (n=19) and grade III (n=10) TNBC samples (FIG. 3a, P<0.001). Grade I samples (n=6) showed a trend towards decrease, but were not statistically different to NAT (FIG. 6a). These results indicate that FOSB expression is down regulated during TNBC progression, and suggest that FOSB may be detrimental to TNBC development. We then evaluated whether the induction of FOSB by TP4 is associated with TNBC death. As demonstrated by Western blotting, the increase of FOSB in TNBC cells treated with TP4 is time-dependent (FIG. 6b) and is correlated with the timing of TP4 induced-cell death (FIG. 1a). Transient expression of FOSB or FOSAB (0.1-0.4 μg) in TNBC cells resulted in substantial cell death as compared to the vehicle control, as determined by ATP assay (FIG. 6(c), P<0.001). Interestingly, TNBC cells were more resistant to FOSAB expression than FOSB expression, at high concentration (FIG. 6c, P<0.001). Whether FOSB knock down disrupts TP4-mediated TNBC cell death was determined. FOSB knockdown MB231 cells were generated through transduction with lentiviral particles containing 4 target-specific shRNA constructs (19-25 nucleotides, including the hairpin). The Western blotting data indicated that TP4 treatment caused significant FOSB induction in control cells (P<0.01), but not FOSB knock-down cells (FIGS. 6d, 6e). The results acquired from MTS assay showed that FOSB knockdown significantly protected MB231 cells against TP4-induced death (FIG. 6f). We next investigated whether the molecular composition of AP-1 complexes are influenced by strong induction of FOSB in TNBC cells. It was previously shown that FRA1 is associated with the epithelial-to-mesenchymal transition (EMT) as a key factor involved in TNBC progression[38]; however, the level of FRA1 was not affected by TP4 treatment, as shown by immunoblotting (FIGS. 6g, 6h). Surprisingly, while levels of CDH1 were significantly increased (FIGS. 6g, 6i), levels of other EMT related proteins were unaffected (ZO1, Intergrin α5, Vimentin, αSMA, and SNAI1) (FIG. 6g). We proceeded to determine the activity of each FOS family member. AP-1 activation was quantified by incubating nuclear extracts from TNBC cells treated with or without TP4 with oligonucleotides containing a tetracycline response element (TRE); DNA-protein complexes were subsequently isolated using antibodies against c-FOS, FOSB, FRA1, and c-JUN. In the absence of TP4 (mock control), the signal-to-background ratios of c-FOS, FOSB, FRA1, and c-JUN activation (represented by $OD_{450}$) were 1.4:1, 1.4:1, 3.5:1, and 8.8:1, respectively (FIG. 6j). Cells treated with TP4 exhibited a 1.4 and 2.8 fold increase of c-FOS and FOSB activity, respectively, as compared to mock controls (P=0.0291 and P<0.001) (FIG. 6j); such an increase was not observed for FRA1 (P=0.5593, FIG. 6j). Interestingly, c-JUN activity was decreased by TP4 treatment (P=0.0272) (FIG. 6j).

Figure 6K:
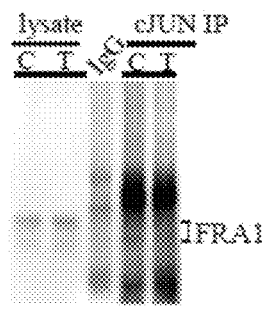
Figure 6L:
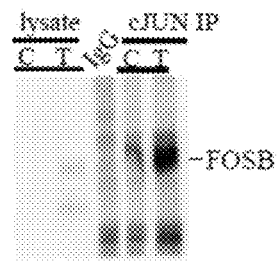

Coimmunoprecipitation of cJUN confirmed an association between c-JUN and FRA1 (FIG. 6k), and the cJUN-FOSB immunocomplex was identified after TP4 treatment of TNBC cells (FIG. 6l). These results suggest that the induction of FOSB by TP4 in TNBC cells possibly alters AP-1 complex composition and thereby causes cell death.

TP4 Causes Mitochondrial Dysfunction

Figure 7A:
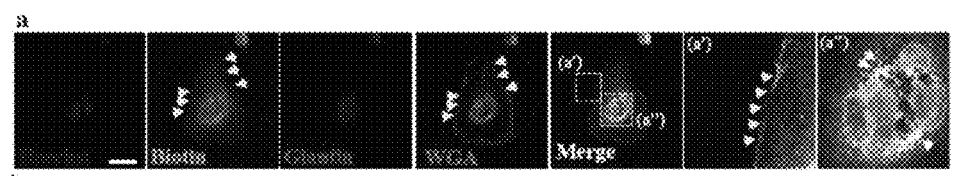
FIGS. 7a-7h show that TP4 is targeted to the TNBC cell membrane and intracellular organelles.
Figure 7B:
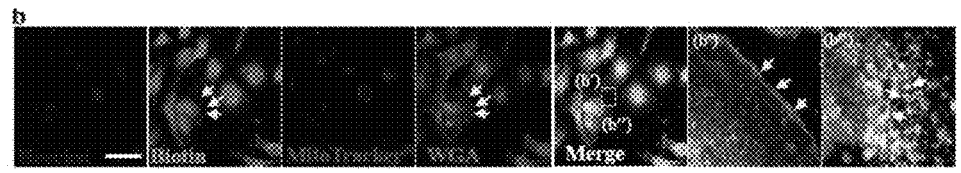
Figure 7C:
Figure 7D:
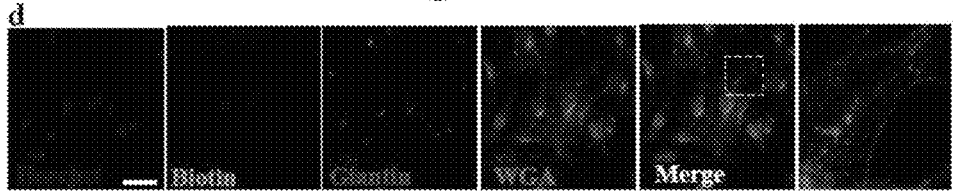
Figure 7E:
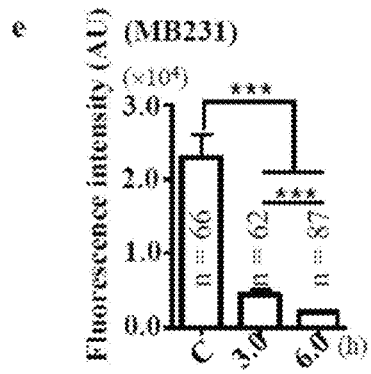
Figure 7G:
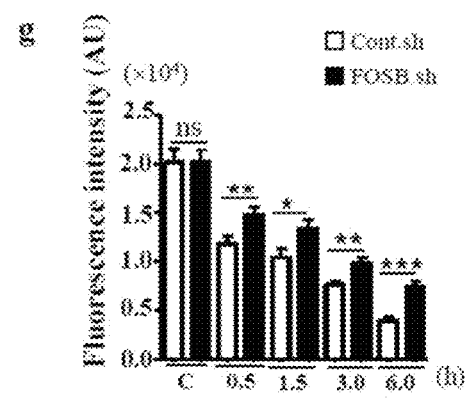
Figure 7F:
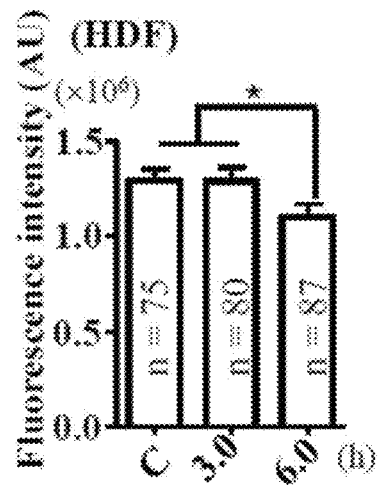
Figure 7H:
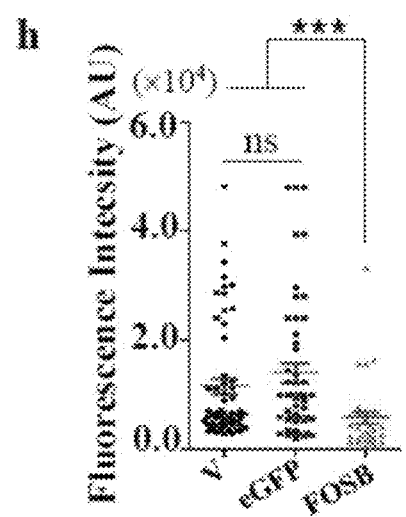
Figure 8A:
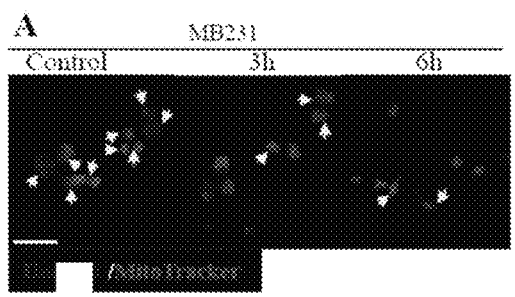
FIGS. 8A-8G show the mitochondrial dysfunction caused by TP4 treatment through FOSB induction.
Figure 8B:
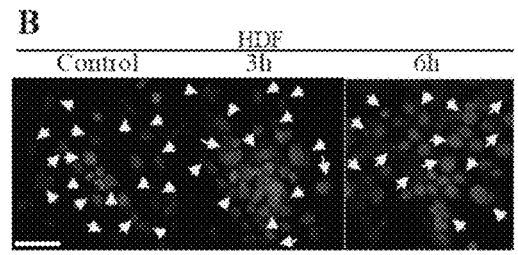
Figure 8C:
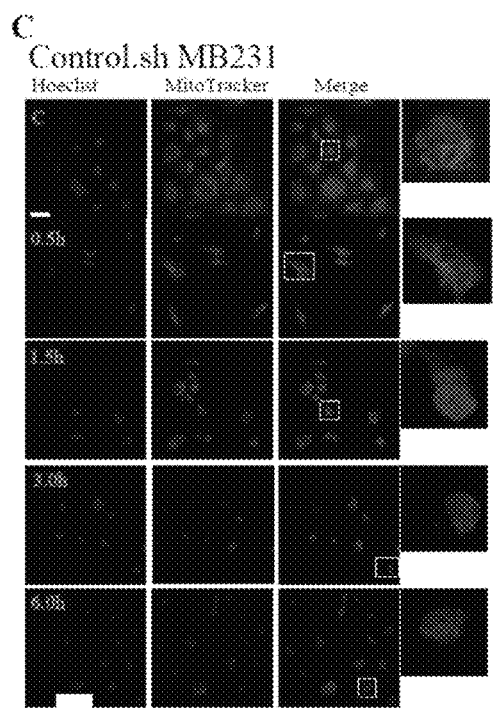
Figure 8D:
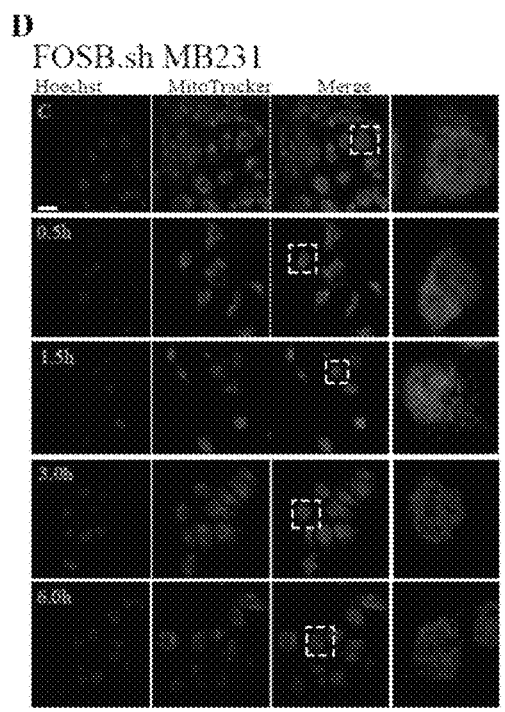
Figure 8E:
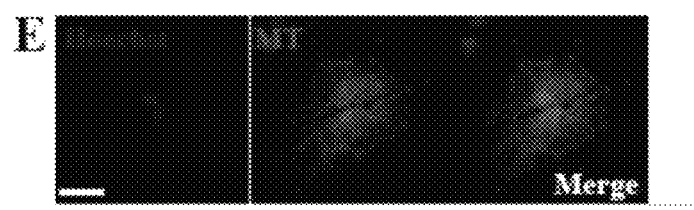
Figure 8F:
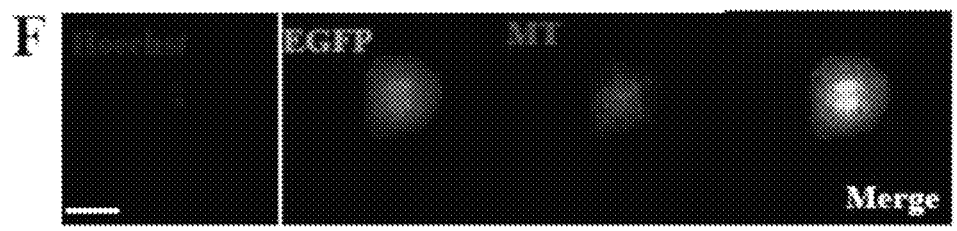
Figure 8G:
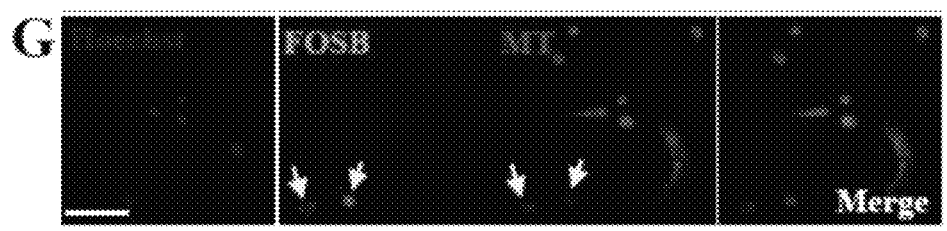

To characterize the mechanism of action of TP4 and the role of FOSB induction, we examined the cellular localization of TP4 in TNBC cells. Cells treated with biotinylated TP4 (14 μg $mL^{-1}$) for 1 h were co-stained with biotin, organelle-specific antibodies/dye (Calreticulin for the ER; Giantin for the Golgi; and MitoTracker for the mitochondria), and fluorescent dye-conjugated WGA (for the plasma membrane). TP4 was observed to be targeted to the Golgi, mitochondria, and plasma membrane as evidenced by strong co-localization of the biotin signal with Giantin (FIG. 7a, indicated by white arrows), MitoTracker (FIG. 4b, indicated by white arrows), and WGA (FIGS. 7a-7c, indicated by yellow arrows), but not with the ER (FIG. 7c). Importantly, only weak background staining against biotin was observed in the nuclei of the HDF control (FIG. 7d), suggesting that normal cell membranes are unlikely to be targeted by TP4. The observation that TP4 is selectively targeted to the mitochondria led us to examine whether TP4-mediated BC toxicity is associated with mitochondrial dysfunction. Immunocytochemical staining through potential-dependent accumulation of MitoTracker revealed a significant loss of mitochondrial membrane potential in TNBC cells at 3 and 6 h post-TP4 treatment as compared to the control group (P<0.001) (FIG. 7e and FIG. 8A), while no significant difference was observed for HDF cells (FIG. 7f and FIG. 8B). We next investigated whether FOSB induction contributes to the loss of mitochondrial membrane potential in TNBC cells. FOSB knockdown partially prevented the loss of mitochondrial membrane potential in response to TP4 treatment as compared to the control cells (FIG. 7g and FIGS. 8C and 8D). Interestingly, FOSB-transfected cells showed a significant loss of mitochondrial membrane potential compared to un-transfected control or vector transfected control (FIG. 7h and FIGS. 8E-8G). It was suggested that TP4 induces a loss of mitochondrial membrane potential prior to FOSB induction; subsequent FOSB induction may further contribute to mitochondrial dysfunction.

2.4 Mitochondrial Calcium Leakage Caused by TP4 Induces FOSB

It was shown in Ting that CAP induces AP-1 to trigger cancer cell death through calcium signaling (Ting et al.). We next examined whether $Ca^{2+}$ homeostasis is affected by TP4 treatment in TNBC cells. Intracellular $Ca^{2+}$ levels were measured using fluo-4 AM $Ca^{2+}$ indicators at 5-30 min after treatment of TNBC cells with TP4 (FIG. 9a). A significant increase in the $Ca^{2+}$ levels of cells treated with 5-20 μg $mL^{-1}$ TP4 for 5 min as compared to the mock control (P<0.001) was observed, indicating that TP4 treatment altered $Ca^{2+}$ homeostasis in TNBC cells. However, it is likely that TP4 does not target the ER (FIG. 7c), the intracellular $Ca^{2+}$ store, but instead targets the mitochondria (FIGS. 7a, 7b), which takes up $Ca^{2+}$ released from the ER, suggesting that the increase of intracellular $Ca^{2+}$ may be due to leakage from mitochondria. We tested this possibility by using a mitochondrial $Ca^{2+}$ indicator, Rhod-2 AM, to dynamically monitor the $Ca^{2+}$ level upon TP4 treatment. We observed that the $Ca^{2+}$ levels in cells treated with 5-20 μg $mL^{-1}$ TP4 for 30 min exhibited a trend towards decrease as compared to the mock control (P<0.001), indicating that TP4 treatment disrupted $Ca^{2+}$ dynamics in mitochondria (FIG. 9b). In addition, we addressed whether TP4-induced Ca'-mediated stress responses cause downstream FOSB induction. Pre-treatment of TNBC cells with BAPTA/AM, a $Ca^{2+}$ chelator, prior to TP4 treatment disrupted FOSB induction and TP4-mediated TNBC cell death, as compared to the mock control (FIGS. 9c-9e). Moreover, application of AIP2, a calcium/calmodulin-dependent protein kinase (CaMK) II inhibitor, to block Ca'-mediated downstream signaling resulted in a trend towards decrease, but not complete block, of FOSB induction compared to mock control (FIGS. 9f, 9g) and partly prevented TP4-induced TNBC cell death (FIG. 9h). Overall, these results indicate that TP4 is targeted to the mitochondria, disrupts $Ca^{2+}$ homeostasis, and ultimately induced downstream FOSB to mediate TNBC cell death (FIG. 9i).

2.5 TP4 Inhibits Tumor Growth in a Nude Mouse Xenograft Model

Figure 10A:
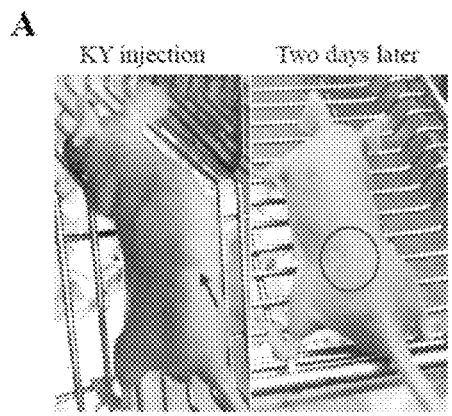
FIGS. 10A-10B show that KY jelly was well-absorbed in null mice.
Figure 10B:
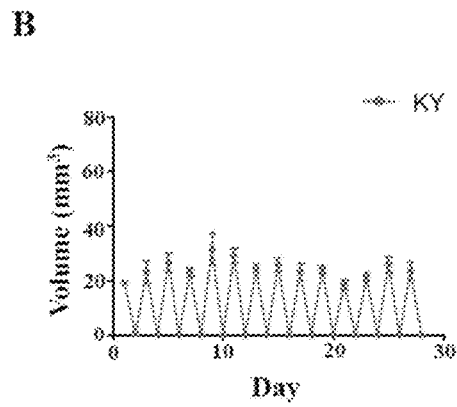
Figure 11A:
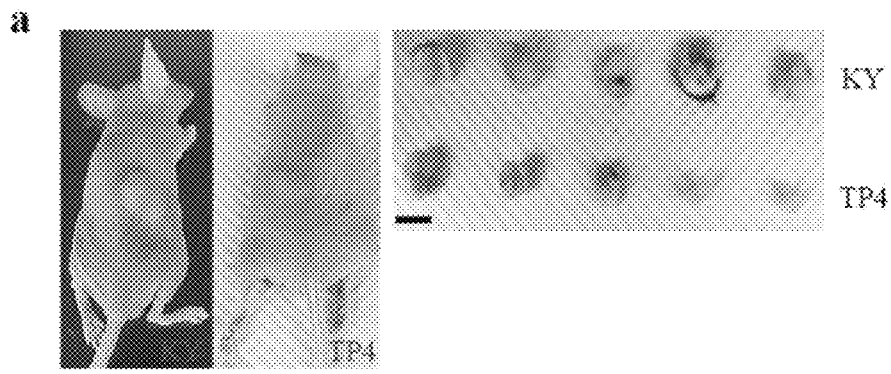
FIGS. 11a-11e show that TP4 inhibited TNBC xenograft growth in nude mice.
Figure 11B:
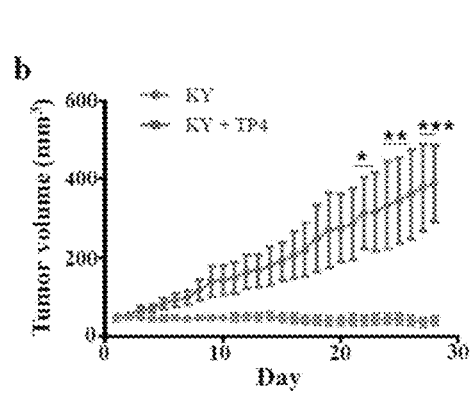
Figure 11C:
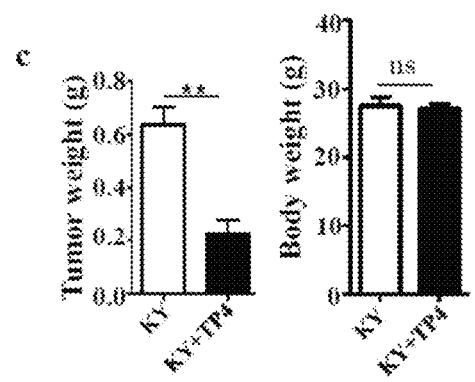
Figure 11D:
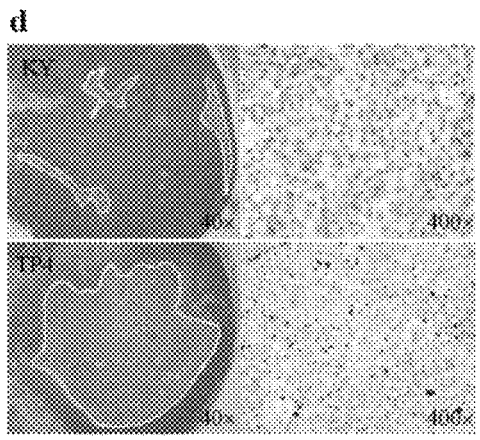
Figure 11E:
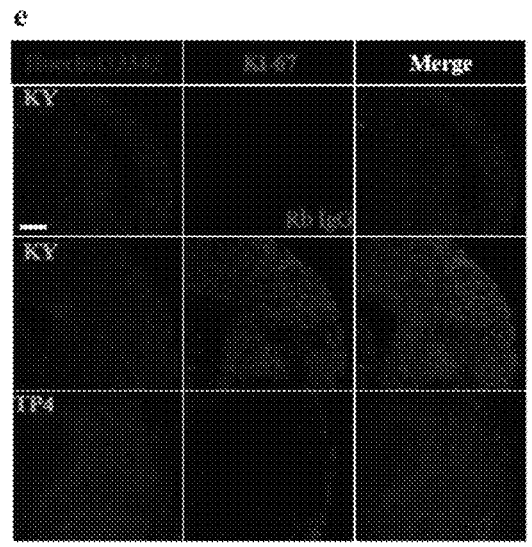

To evaluate the effects of TP4 treatment on tumor growth in vivo, transplanted TNBC cells were subcutaneously injected into nude mice (n=5), and tumor growth was assessed daily for 28 days. A group of nude mice with xenografts were treated with TP4 every two days once the tumor reached a certain size. As shown in FIG. 10, KY jelly was well-absorbed in null mice. (FIG. 10A), and nude mice (n=5) were subcutaneously injected with 10 μL KY jelly plus 50 μL distilled water every two days for a total of fourteen injections. The size of the injection mixture was calculated every two days, and the results were shown in FIG. 10(B). Results represent the mean±SEM. Significant differences in tumor growth between control (KY jelly alone) and TP4 (KY jelly plus TP4)-treated groups were observed (P<0.001) (FIGS. 11a, 11b). TP4-treated tumors grew into smaller tumor masses than those of control groups (P=0.0017) (FIG. 11c, left), but no significant differences in body weight were observed between each group of mice (FIG. 11c, right). Pathological studies confirmed that a large portion of the central region is necrotic in intratumoral TP4-treated groups (FIG. 11d). A dramatic decrease in cells positive for the proliferation marker Ki-67 was observed in tumor tissue sections from TP4-treated groups, paralleling the macroscopic findings (FIG. 11e); collectively, these results indicate that TP4 kills TNBC cells in vivo.

2.6 TP4 Prolongs the Survival of TNBC Xenograft Zebrafish

Figure 12:
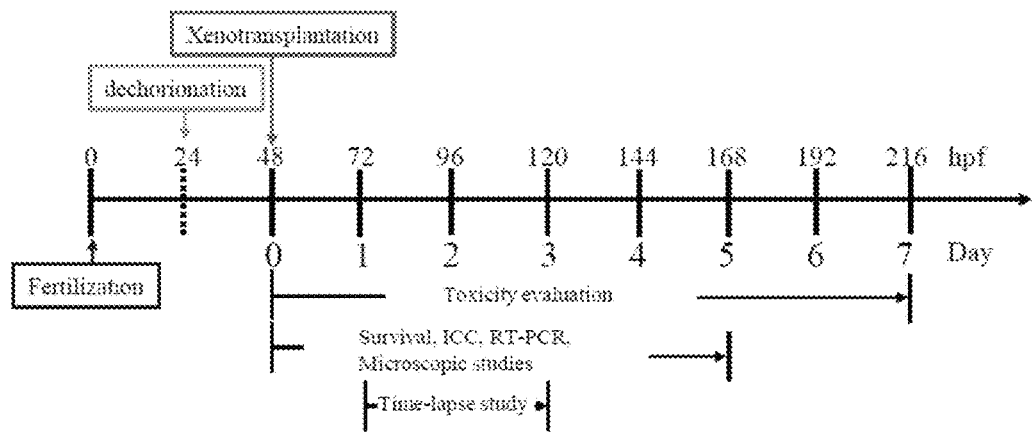
FIG. 12 provides a schematic diagram outlining the design of the zebrafish xenograft study. Experiments conducted in zebrafish embryos at 48 h were shown.
Figure 13:
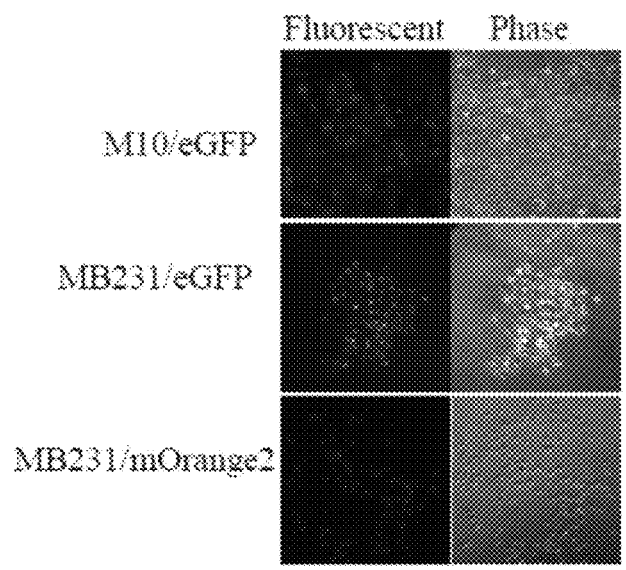
FIG. 13 shows the generation of fluorescent reporter cell-lines. Fluorescent stable clones (eGFP-expressing M10 or eGFP/mOrang2-expressing MB231 cells) were acquired under G418 or puromycin selection. Single clones were manipulated, expanded, and used for xenotransplantation.

To further investigate the therapeutic ability of TP4, we generated a TNBC xenograft zebrafish model with which to study the ability of TP4 to inhibit TNBC migration and invasion. A schematic indicating the treatment procedures and analytic approaches used in this study is shown in FIG. 12. Fluorescence reporter TNBC cell-lines were first obtained by transfection of M10 or TNBC cells with eGFP or mOrange2 expression vectors, followed by antibiotic selection (FIG. 13). Survival analysis at 48 hours post-fertilization (hpf) revealed no obvious toxic effects of injection of non-tumorigenic eGFP-expressing M10 cells (800-

Figure 14A:
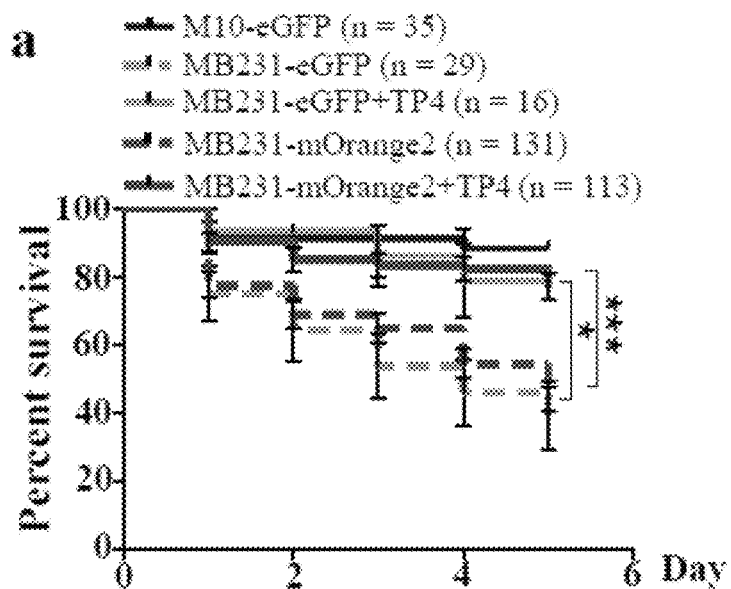
FIGS. 14a-14j show that TP4 treatment prolonged survival in TNBC xenograft zebrafish.
Figure 14B:
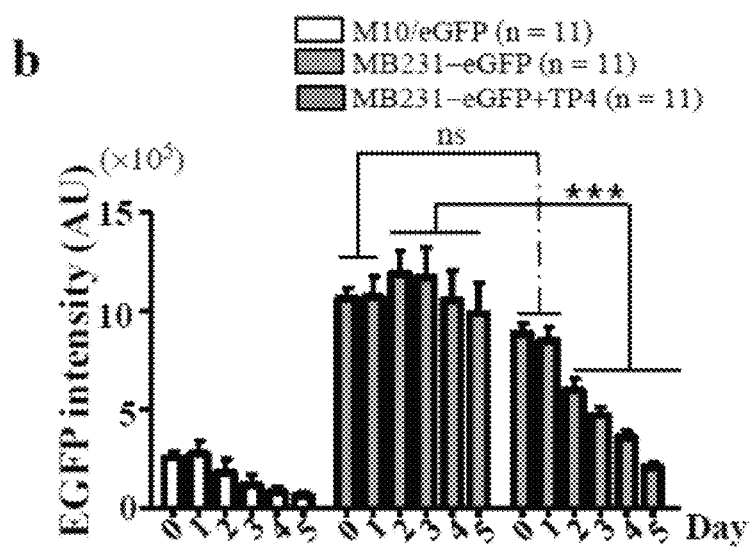
Figure 14C:
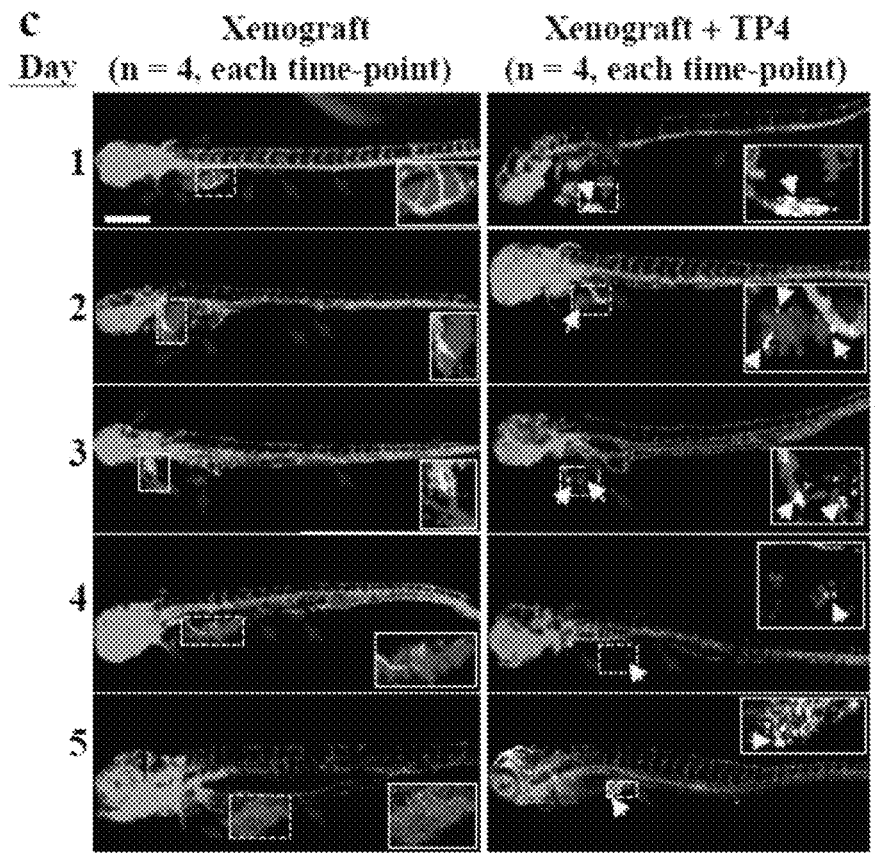
Figure 14D:
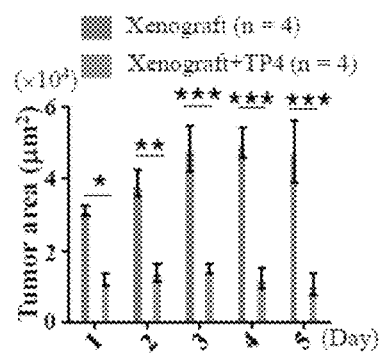
Figure 14E:
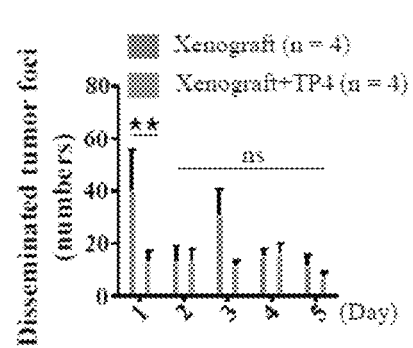
Figure 14F:
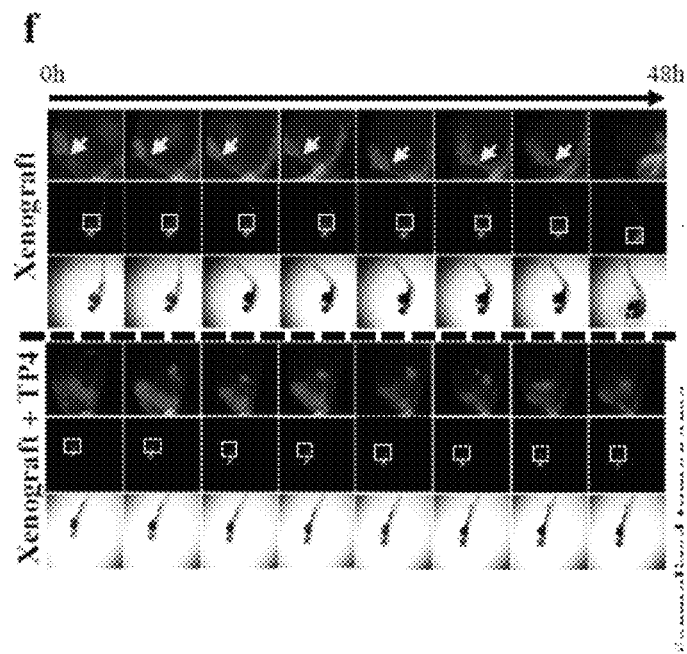
Figure 14G:
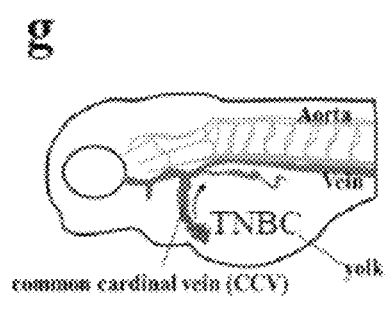
Figure 14H:
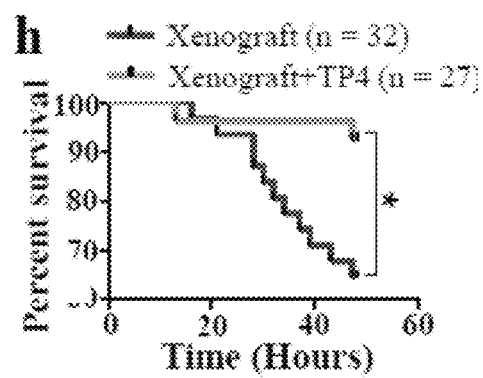
Figure 14I:
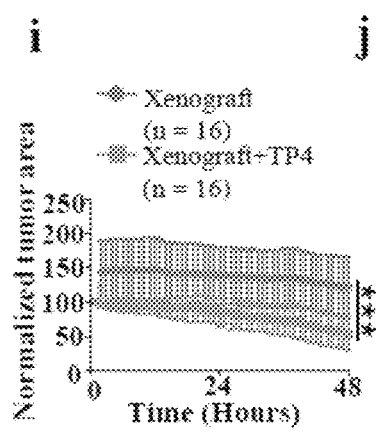
Figure 14J:
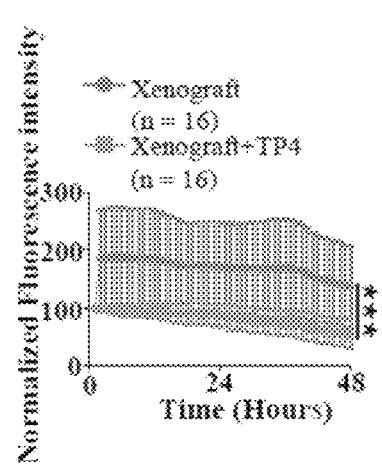
Figure 15A:
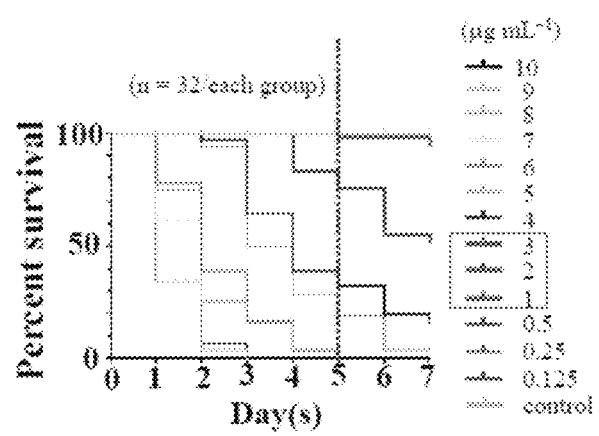
FIGS. 15A-15C show the toxicity and therapeutic efficacy evaluation of TP4 in zebrafish embryos.
Figure 15B:
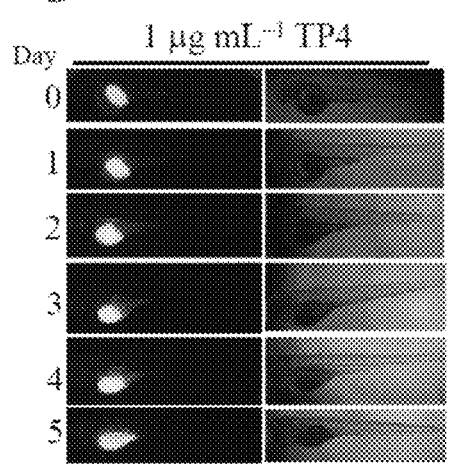
Figure 15C:
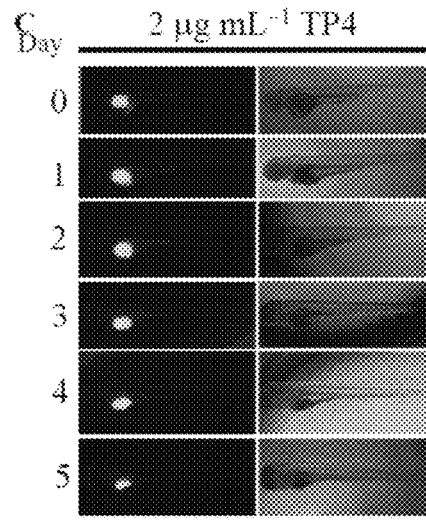

1,200 cells per embryo, zebrafish survival rate >90%, FIG. 14a). In contrast, injection of eGFP- and mOrange2-expressing TNBC xenografts showed an unexpected increase in zebrafish embryo mortality at 168 hpf to about 38.3% and 44.8%, respectively (FIG. 14a). Before evaluating the therapeutic activity of TP4, we examined TP4 toxicity in zebrafish. Serial dilutions of TP4 (0.125 ng mL$^{-1}$-20 μg mL$^{-1}$) were added to the zebrafish culture medium; we observed that TP4 doses of 1 and 2 μg mL$^{-1}$ had no obvious toxic effects on normal zebrafish (FIG. 15A). However, further testing revealed poor therapeutic efficacy of these doses in eGFP-expressing TNBC xenograft zebrafish (FIGS. 15B, 15C). As most wild-type zebrafish (>75%) treated with 3 μg mL$^{-1}$ (1.01 μM) TP4 were still viable at 168 hpf (FIG. 15A), we used this dose in subsequent experiments. TP4 (3 μg mL$^{-1}$, administered daily) treatment significantly prolonged survival of eGFP- and mOrange2-TNBC xenograft zebrafish (78.9% and 82.5%) in comparison with mock-treated groups (P=0.0149 and P<0.0001, respectively) (FIG. 14a). The therapeutic efficacy of TP4 in a single xenograft zebrafish was determined by quantitation of the eGFP fluorescent signal through days 0-5 (48-168 hpf). In control M10 xenograft zebrafish, the eGFP fluorescent signal exhibited a gradual trend towards decrease; however, such a trend was not observed in TNBC xenograft zebrafish (FIG. 14b, left and center). In the TP4-treated groups, the eGFP fluorescent intensity was significantly decreased through days 2-5 in comparison with the mock control (P<0.001), indicating a positive therapeutic effect of TP4 in vivo (FIG. 14b). To address the mechanism underlying TP4-mediated therapeutic activity, we performed whole-mount staining to determine whether TP4 treatment exerted any TNBC cell-autonomous effects. We report that TNBC cells in the TP4-treated group, but not the mock-treated group, presented with positive FOSB staining (FIG. 14c). In addition, the xenograft tumor area (P<0.05 compared to the non-treated group) and the numbers of disseminated tumor foci (P<0.01 at day 1 compared to the non-treated group) were decreased upon TP4 treatment (FIGS. 14d, 14e). Together, these results indicate that TP4 may contribute to autonomous elimination of TNBC through FOSB induction. We also investigated whether any non-TNBC cell autonomous effects induced by TP4 benefit cancer cell elimination in vivo. To this end, the expression profiles of certain genes involved in innate immunity against some pathogen infections in zebrafish embryo were determined by qPCR (van der Vaart et al., Pathogen recognition and activation of the innate immune response in zebrafish. *Advances in hematology*, 159807. 2012). We observed that application of TP4 (3 μg mL$^{-1}$, administered daily) to wildtype zebrafish generally resulted in a significant decrease of immune gene expression over time (FIGS. 16A-16G, left), except at some specific time-points (Il8 increased at Day 1 and Il10/Ifnφ1 increased at day 5); however, TP4 treatment had no significant effects on Tnfα expression (FIG. 16E, left) as compared with the un-treated control. In TNBC xenograft zebrafish embryos, TP4 treatment was observed to significantly enhance immune responsive gene expression at around day 2 (FIGS. 16A-16G, right) as compared to un-treated groups. These results suggest that TP4 may enhance innate immunity in TNBC xenograft zebrafish embryos. Furthermore, the finding that TNBC xenografts enhance mortality in zebrafish led us to further investigate the mechanisms involved through high-content imaging. Time-lapse imaging revealed that TNBC cells migrated and invaded developed blood vessels, causing substantial abdominal edema, curvature of the trunk, and death (FIGS. 14f, 14g). TNBC xenograft zebrafish that received a single treatment of TP4 (3 μg mL$^{-1}$) exhibited prolonged survival in comparison with the non-treated group (92.6% vs 65.6%, P<0.05) (FIG. 14(h)), and also contained reduced quantities of TNBC, as revealed by a gradual decrease in xenograft TNBC tumor area (FIG. 14i) and fluorescence intensity (FIG. 14j). These findings indicate that TNBC metastasis and invasion are possibly a major cause of zebrafish death, and that TP4 treatment eliminates TNBC growth in vivo.

Given the above, it was concluded that TP4 is a potential medicament for treating breast cancer.

The descriptions and claims as provided should be understood as of demonstrative purpose instead of limitative in any way to the scope of the present invention.

We claim:

1. A method for treating a breast cancer or a triple negative breast cancer (TNBC) in a subject, comprising administering to the subject a composition comprising a therapeutically effective amount of tilapia piscidin 4 (TP4), together with a pharmaceutically acceptable carrier.

2. The method of claim 1, wherein TP4 may be a functional fragment or variant of TP4.

* * * * *